United States Patent
Burris et al.

(10) Patent No.: US 6,908,908 B2
(45) Date of Patent: *Jun. 21, 2005

(54) BIOLOGICALLY ACTIVE 4H-BENZO [1,4] OXAZIN-3-ONES

(75) Inventors: Thomas P. Burris, Noblesville, IN (US); Donald W. Combs, Neptune City, NJ (US); Philip J. Rybczynski, Branchburg, NJ (US); Joseph Dudash, Jr., Hillsborough, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/990,461

(22) Filed: Nov. 21, 2001

(65) Prior Publication Data

US 2003/0083329 A1 May 1, 2003

Related U.S. Application Data

(63) Continuation-in-part of application No. 09/854,302, filed on May 11, 2001, now Pat. No. 6,555,536.
(60) Provisional application No. 60/203,860, filed on May 12, 2000.

(51) Int. Cl.[7] .................... A61K 31/538; C07D 265/36
(52) U.S. Cl. ................. 514/80; 514/230.5; 544/105
(58) Field of Search .................. 544/105; 514/230.5, 514/80

(56) References Cited

U.S. PATENT DOCUMENTS 6,555,536 B2 * 4/2003 Burris et al. ............. 514/230.5

FOREIGN PATENT DOCUMENTS

| JP | 09 012575 A | 1/1997 |
| WO | WO 91 19702 A | 12/1991 |
| WO | WO 96 04260 A | 2/1996 |
| WO | WO 97 17333 A | 5/1997 |
| WO | WO 97 28167 A | 8/1997 |
| WO | WO 99 20614 A | 4/1999 |
| WO | PCT/US 01/15383 | 5/2001 |

OTHER PUBLICATIONS

Hilliard, Jamese J. et. al., "Multiple mechanisms of action for inhibitors of histidine protein kinases from bacterial two–component systems" Antimicrob. Agents Chemother. (1998), 43(7), 1693–1699, XP002171516 the whole document, especially p. 1695, FIG. 1.

* cited by examiner

*Primary Examiner*—Richard L. Raymond
(74) *Attorney, Agent, or Firm*—Ellen Ciambrone Coletti; Evelyn D. Shen; Jeremy K. McKown

(57) ABSTRACT

The invention is directed to 4h-benzo[1,4]oxazin-3-ones useful as peroxisome proliferator activated receptor gamma (PPARγ) agonists or antagonists. Pharmaceutical compositions comprising compounds of the present invention and methods of treating conditions such as NIDDM and obesity are also disclosed.

19 Claims, No Drawings

BIOLOGICALLY ACTIVE 4H-BENZO [1,4] OXAZIN-3-ONES

CROSS REFERENCE TO RELATED APPLICATIONS

This application is a continuation-in-part of U.S. Ser. No. 09/854,302, filed May 11, 2001, now U.S. Pat. No. 6,555,536 which in turn claims priority from U.S. Ser. No. 60/203,860, filed May 12, 2000.

FIELD OF THE INVENTION

This invention relates to novel 4H-benzo[1,4]oxazin-3-ones useful for the treatment of Non-Insulin Dependant Diabetes Mellitus (NIDDM) and complications thereof and disorders related to lipid metabolism and energy homeostasis such as obesity. More particularly, the compounds act through the peroxisome proliferator activated receptor gamma (PPARγ). Compounds in the series are PPARγ modulators.

BACKGROUND OF THE INVENTION

Diabetes is a disease caused by multiple factors and characterized by hyperglycemia which may be associated with increased and premature mortality due to an increased risk for microvascular and macrovascular diseases such as nephropathy, neuropathy, retinopathy, atherosclerosis, polycystic ovary syndrome (PCOS), hypertension, ischemia, stroke, and heart disease. Type I diabetes (IDDM) results from genetic deficiency of insulin, the hormone regulating glucose metabolism. Type II diabetes is known as non-insulin dependent diabetes mellitus (NIDDM), and is due to a profound resistance to insulin regulatory effect on glucose and lipid metabolism in the main insulin-sensitive tissues, i.e., muscle, liver and adipose tissue. This insulin resistance or reduced insulin sensitivity results in insufficient insulin activation of glucose uptake, oxidation and storage in muscle and inadequate insulin repression of lipolysis in adipose tissue as well as glucose production and secretion in liver. Many Type II diabetics are also obese, and obesity is believed to cause and/or exacerbate many health and social problems such as coronary heart disease, stroke, obstructive sleep apnoea, gout, hyperlipidemia, osteoarthritis, reduced fertility, and impaired psychosocial function.

A class of compounds, thiazolidinediones (glitazones), have been suggested to be capable of ameliorating many symptoms of NIDDM by binding to the peroxisome proliferator activated receptor (PPAR) family of receptors. They increase insulin sensitivity in muscle, liver and adipose tissue in several animal models of NIDDM resulting in correction of the elevated plasma levels of glucose, triglycerides and nonesterified free fatty acids without any occurrence of hypoglycemia. However, undesirable effects have occurred in animal and/or human studies including cardiac hypertrophy, hemadilution and liver toxicity.

Most PPARγ agonists currently in development have thiazolidinedione ring as their common chemical structure. PPARγ agonists have been demonstrated to be extremely useful for the treatment of NIDDM and other disorders involving insulin resistance. Recently, troglitazone, rosiglitazone, and pioglitazone have been approved for treatment of type II diabetes. There is also indication that benzimidazole-containing thiazolidinedione derivatives may be used to treat irritable bowel disorder (IBD), inflammation, and cataract (JP 10195057).

JP 09012576 (Yoshitake et al.) discloses benzothiazine derivatives stated as useful therapeutic agents for circulatory system disease and glaucoma.

JP 09012575 (Hiroaki et al.) discloses benzoxazine and benzothiazine derivatives stated to be useful as prophylactic drugs and/or therapeutic drugs in hyperlipemia, hyperglycemia, obesity, diseases attributable to sugar tolerance insufficiency, hypertension, osteoporosis, cachexia, and complications of diabetes such as retinopathy, nephrosis, neuropathy, cataract, coronary artery disease and arteriosclerosis.

WO 99/20614 (Lohray et al.) discloses β-aryl-α-oxysubstituted alkylcarboxylic acids stated as antiobesity and hypocholesterolemic compounds which may have agonist activity against PPARα and/or PPARγ, and optionally inhibit HMG CoA reductase.

WO 97/17333 (Frechette et al.) and U.S. Pat. Nos. 5,696,117 and 5,854,242 to Frechette et al. disclose benzoxazine and pyrido-oxazine compounds having a moiety of a fused phenyl or fused pyridyl, pharmaceutical compositions containing the compounds, and methods for their production and their use in treating bacterial infections.

U.S. Pat. No. 5,859,051 to Adams et al. discloses the following acetylphenols,

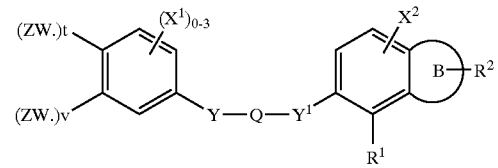

wherein substituents are as described in the reference, which are stated to be useful as antiobesity and antidiabetic compounds without the thiazolidinedione moiety.

WO 99/38845 (De La Brouse-Elwood et al.) discloses the following compounds,

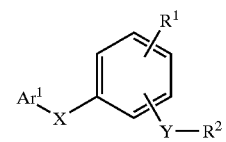

wherein substituents are as described in the reference, which are stated to modulate the PPARγ receptor and are stated as useful in the diagnosis and treatment of type II diabetes (and complications thereof) and inflammatory disorders.

SUMMARY OF THE INVENTION

The present invention is directed to a compound of Formula I,

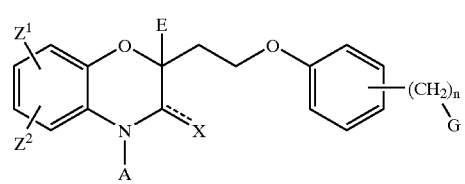

or an optical isomer, enantiomer, diastereomer, racemate or racemic mixture thereof, ester, prodrug form, or a pharmaceutically acceptable salt thereof, wherein A is selected from aryl, heterocyclyl, and $C_1$–$C_{10}$ alkyl, said aryl, heterocyclyl, and $C_1$–$C_{10}$ alkyl being optionally substituted with one or more members selected from the group consiting of halogen, OH, aryl, $C_3$–$C_8$ cycloalkyl, $C_1$–$C_{10}$ alkyl substituted with a halogen, $C_1$–$C_{10}$ alkyl ether, heterocyclyl, carbonyl, oxime, —N($R^1$) ($SO_2R$), —C($NNR^3R^4$) $R^1$, —COO$R^1$, —CON$R^1R^2$, —OC(O)$R^1$, —OC(O)O$R^1$, —OC(O)N$R^1R^2$, —N$R^1R^2$, —N$R^3$C(O)R, —N$R^3$C(O)O$R^1$, and —N$R^3$C(O)N$R^1R^2$, wherein R is selected from $C_1$–$C_6$ alkyl, trifluoromethyl, phenyl, and substituted phenyl;

$R^1$ and $R^2$ are independently selected from hydrogen, $C_1$–$C_{10}$ alkyl, aryl, heterocyclyl, and alkylaryl, or $R^1$ and $R^2$ may be taken together to form a 5- to 10-member ring; and $R^3$ and $R^4$ are independently selected from hydrogen, $C_1$–$C_{10}$ alkyl, aryl, heterocyclyl, alkylaryl, —C(O)$R^1$, or —C(O)N$R^1R^2$;

$Z^1$ is selected from hydrogen, $C_1$–$C_6$ alkyl, aryl, heterocyclyl, COO$R^1$, CON$R^1R^2$, OH, $C_1$–$C_6$ alkyl ether, —OC(O)R, —OC(O)O$R^1$, —OC(O)N$R^1R^2$, —N$R^1R^2$, —N$R^3$C(O)$R^1$, —N$R^3$C(O)O$R^1$, —N$R^3$C(O)N$R^1R^2$, halogen, —C(O)$R^1$, —C(N$R^3$)$R^1$, C(NO$R^3$)$R^1$, and —C(NN$R^3R^4$) $R^1$;

$Z^2$ is selected from hydrogen, halogen, $C_1$–$C_6$ alkyl;

$Z^1$ and $Z^2$ may together form a fused aromatic ring;

n is an integer from 0 to 3;

G is selected from —COO$R^1$, —C(O)COO$R^1$, —CON$R^1R^2$, —CF$_3$, —P(O) (O$R^1$) (O$R^2$), —S—$R^8$, —O—$R^8$,

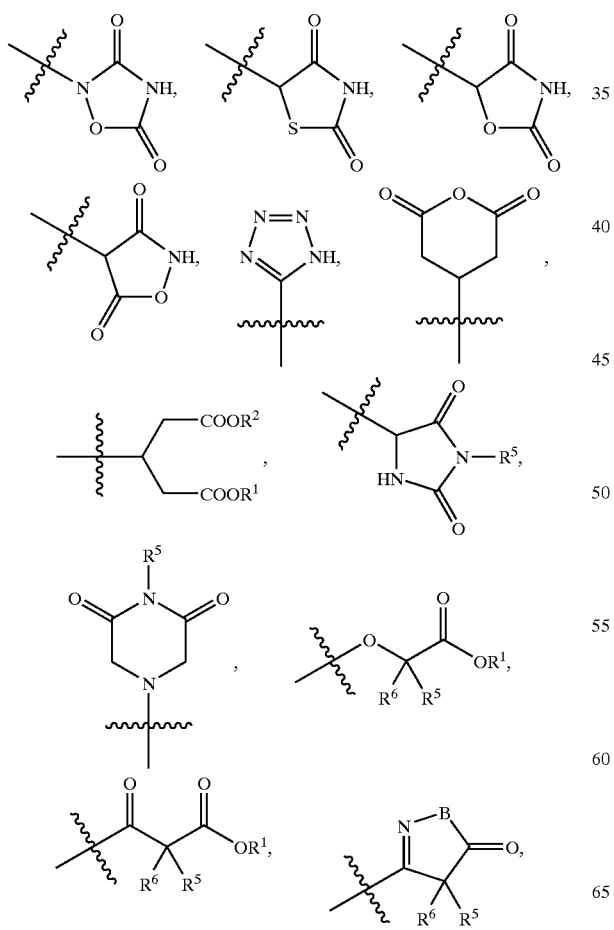

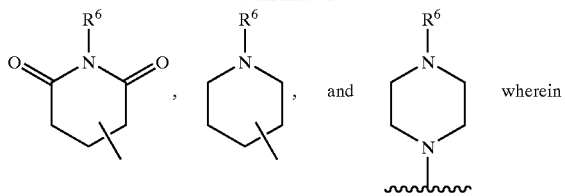

$R^5$ and $R^6$ are independently hydrogen or $C_1$–$C_6$ alkyl;
$R^7$ is hydrogen, $C_1$–$C_6$ alkyl, or —C(O)$R^5$;
$R^8$ is selected from the group consisting of hydrogen, $C_1$–$C_6$ alkyl, and substituted $C_1$–$C_6$ alkyl; and
B is oxygen or —N$R^5$;
E is selected from hydrogen, $C_1$–$C_6$ alkyl and a moiety of the formula

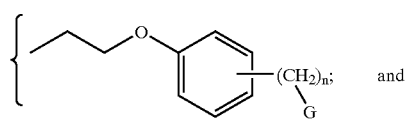

X is hydrogen or oxygen, with the proviso that
when E is hydrogen and G is —COOH, —COOCH$_3$, or a moiety of the formula of

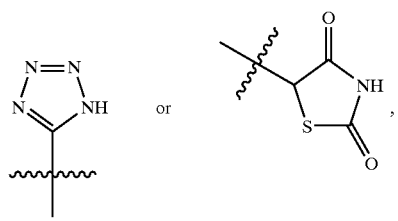

A is selected from the group consisting of aryl, heterocyclyl, substituted $C_1$–$C_6$ alkyl and $C_7$–$C_{10}$ alkyl, provided that when X is hydrogen, n is 1 and G is a moiety of the formula of

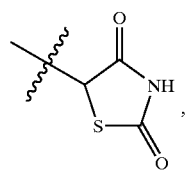

A is selected from the group consisting of heterocyclyl, and $C_7$–$C_{10}$ alkyl.

The compounds of the present invention are PPARγ modulators useful for the treatment of NIDDM and complications thereof and disorders related to lipid metabolism and energy homeostasis such as obesity.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

An embodiment of the invention is a method of treating a subject suffering from a disorder in glucose and lipid metabolism, which comprises administering to the subject a therapeutically effective amount of a compound of Formula I.

Another embodiment of the invention is a method of inhibiting the onset of a condition of a disorder in glucose and lipid metabolism, which comprises administering to the subject a prophylactically effective dose of a compound of Formula I.

Further illustrating the invention is a method of treating a subject suffering from a disorder in glucose and lipid metabolism, which comprises administering to said subject an effective amount of a compound of Formula I, or an optical isomer, enantiomer, diastereomer, racemate or racemic mixture thereof, ester, prodrug form, or a pharmaceutically acceptable salt thereof, wherein said disorder is selected from NIDDM, obesity, nephropathy, neuropathy, retinopathy, atherosclerosis polycystic ovary syndrome, hypertension, ischemia, stroke, heart disease, irritable bowel disorder, inflammation, and cataract.

Also included in the invention is the use of any of the compounds described above for the preparation of a medicament for treating a condition selected from NIDDM, obesity, nephropathy, neuropathy, retinopathy, atherosclerosis polycystic ovary syndrome, hypertension, ischemia, stroke, heart disease, irritable bowel disorder, inflammation, and cataract in a subject in need thereof.

DETAILED DESCRIPTION OF THE INVENTION

The present invention provides 4H-benzo[1,4]oxazin-3-ones of Formula I,

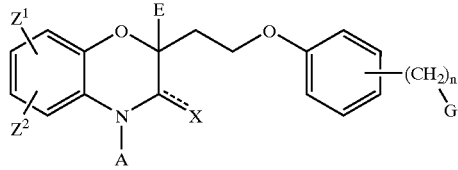

or an optical isomer, enantiomer, diastereomer, racemate or racemic mixture thereof, ester, prodrug form, or a pharmaceutically acceptable salt thereof, wherein A is selected from aryl, heterocyclyl, and $C_1$–$C_{10}$ alkyl, said aryl, heterocyclyl, and $C_1$–$C_{10}$ alkyl being optionally substituted with one or more members selected from the group consisting of halogen, OH, aryl, $C_3$–$C_8$ cycloalkyl, $C_1$–$C_{10}$ alkyl substituted with a halogen, $C_1$–$C_{10}$ alkyl ether, heterocyclyl, carbonyl, oxime, —N($R^1$)($SO_2R$), —C($NNR^3R^4$)$R^1$, —COOR$^1$, —CONR$^1R^2$, —OC(O)R$^1$, —OC(O)OR$^1$, —OC(O)NR$^1R^2$, —NRR$^1R^2$, —NR$^3$C(O)R$^1$, —NR$^3$C(O)OR$^1$, and —NR$^3$C(O)NR$^1R^2$, wherein R is selected from $C_1$–$C_6$ alkyl, trifluoromethyl, phenyl, and substituted phenyl;

$R^1$ and $R^2$ are independently selected from hydrogen, $C_1$–$C_{10}$ alkyl, aryl, heterocyclyl, and alkylaryl, or $R^1$ and $R^2$ may be taken together to form a 5- to 10-member ring; and $R^3$ and $R^4$ are independently selected from hydrogen, $C_1$–$C_{10}$ alkyl, aryl, heterocyclyl, alkylaryl, —C(O)R$^1$, or —C(O)NR$^1R^2$;

$Z^1$ is selected from hydrogen, $C_1$–$C_6$ alkyl, aryl, heterocyclyl, COOR$^1$, CONR$^1R^2$, OH, $C_1$–$C_6$ alkyl ether, —OC(O)R$^1$, —OC(O)OR$^1$, —OC(O)NR$^1R^2$, —NR$^1R^2$, —NR$^3$C(O)R$^1$, —NR$^3$C(O)OR$^1$, —NR$^3$C(O)NR$^1R^2$, halogen, —C(O)R$^1$, —C(NR$^3$)R$^1$, —C(NOR$^3$)R$^1$, and —C(NNR$^3R^4$) R$^1$;

$Z^2$ is selected from hydrogen, halogen, $C_1$–$C_6$ alkyl;

$Z^1$ and $Z^2$ may together form a fused aromatic ring;

n is an integer from 0 to 3;

G is selected from —COOR$^1$, —C(O)COOR$^1$, —CONR$^1R^2$, —CF$_3$, —P(O)(OR$^1$)(OR$^2$), —S—R$^8$, —O—R$^8$,

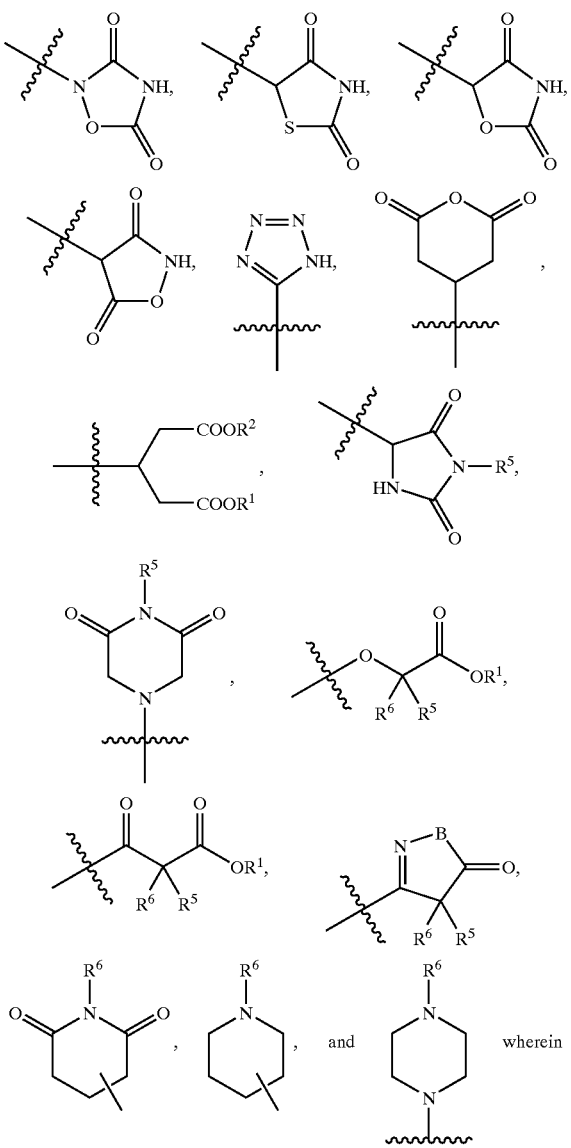

$R^5$ and $R^6$ are independently hydrogen or $C_1$–$C_6$ alkyl;

$R^7$ is hydrogen, $C_1$–$C_6$ alkyl, or —C(O)R$^5$;

$R^8$ is selected from the group consisting of hydrogen, $C_1$–$C_6$ alkyl, and substituted $C_1$–$C_6$ alkyl; and B is oxygen or —NR$^5$;

E is selected from hydrogen, $C_1$–$C_6$ alkyl and a moiety of the formula

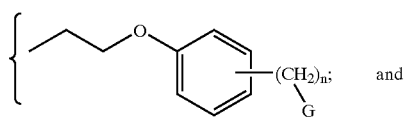

X is hydrogen or oxygen, with the proviso that
when E is hydrogen and G is —COOH, —COOCH₃, or
a moiety of the formula of

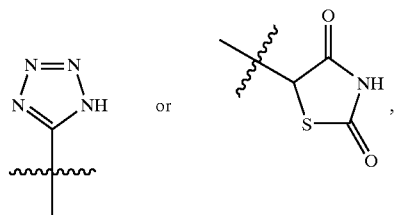

A is selected from the group consisting of aryl,
heterocyclyl, substituted $C_1$–$C_6$ alkyl and $C_7$–$C_{10}$
alkyl, provided that when X is hydrogen, n is 1 and G
is a moiety of the formula of

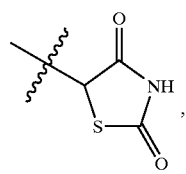

A is selected from the group consisting of heterocyclyl,
and $C_7$–$C_{10}$ alkyl.

Preferably, compounds of Formula I, wherein X is oxygen
are embodiments of the present invention.

Compounds of Formula I wherein E is $C_1$–$C_6$ alkyl or a
moiety of the formula

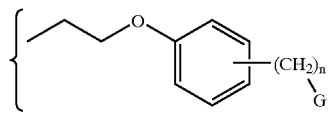

are also preferred embodiments of this invention.

Compounds of Formula I wherein
A is optionally substituted $C_1$–$C_6$ alkyl or optionally
substituted aryl;
X is oxygen; and
G is selected from —COOR¹, —CONR¹R², —CF₃,

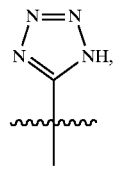

—P(O) (OR¹) (OR²), —S—R⁸, —O—R⁸, and

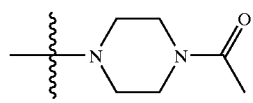

are preferred embodiments of the present invention as well.
Particularly, A is substituted $C_1$–$C_6$ alkyl and G is COOH or
COOCH₃.

The following compounds are still preferred embodiments of the present invention:

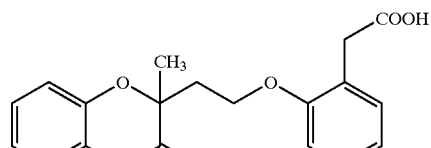

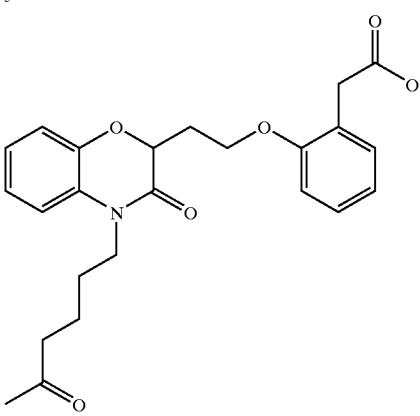

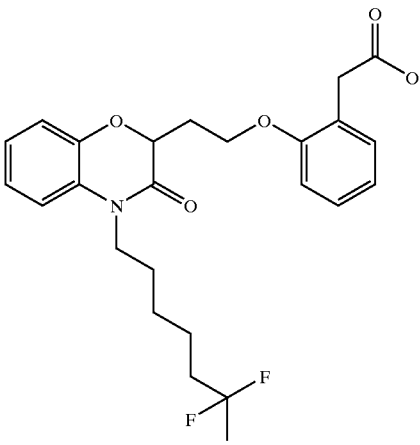

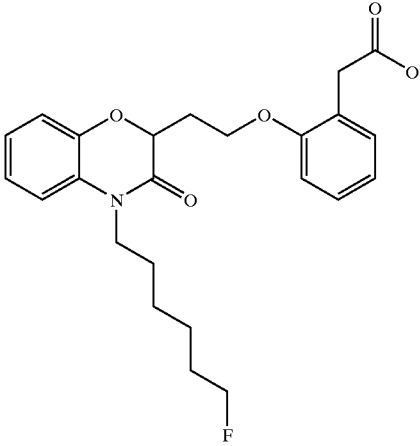

-continued

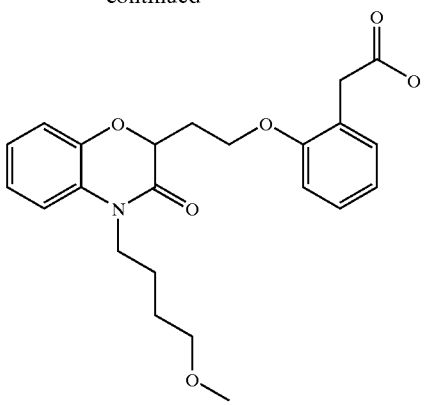

Unless otherwise noted, "alkyl" and "alkoxy" as used herein, whether used alone or as part of a substituent group, include straight and branched chains having 1 to 10 carbon atoms, or any number within this range, optionally substituted with one or more independent groups including, but not limited to, H, halogen (F, Cl, Br, I), $C_1$–$C_{10}$ alkyl, OH, amino, alkoxy, alkthio, aryl, substituted aryl, heterocyclyl, substituted heterocyclyl, $COOR^1$, and $CONR^1R^2$ wherein $R^1$ and $R^2$ are as described above. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl, 2-methylpentyl, and the like. Alkoxy radicals are oxygen ethers formed from the previously described straight or branched chain alkyl groups. Cycloalkyl groups contain 3 to 8 ring carbons and preferably 5 to 7 ring carbons. Similarly, alkenyl and alkynyl groups include straight and branched chain alkenes and alkynes having 1 to 10 carbon atoms, or any number within this range.

The term "Ar" represents aryl. Unless otherwise stated, "aryl," employed alone or in combination with other terms (e.g., aryloxy, arylthioxy, arylalkyl), is an aromatic radical which can be a single ring or multiple rings which are fused together or linked covalently. Illustrative aryl groups may be phenyl or naphthyl optionally substituted with one or more independent groups such as H, halogen, $C_1$–$C_{10}$ alkyl, $C_3$–$C_8$ cycloalkyl, $COOR^1$, $CONR^1R^2$, OH, $C_1$–$C_{10}$ alkyl ether, aryl or heterocyclyl ether, $OC(O)R^1$, $OC(O)OR^1$, $OC(O)NR^1R^2$, $NR^1R^2$, $NR^3C(O)R^1$, $NR^3C(O)OR^1$, and $NR^3C(O)NR^1R^2$ wherein $R^1$ and $R^2$ are as described above. When $Z^1$ and $Z2$ as described above together form a fused aryl ring, the aromatic ring is fused to the phenyl moiety of benzoxazin in Formula I.

"Heterocyclyl" or "heterocycle" is a 3- to 8-member saturated, partially saturated, or unsaturated single or fused ring system which consists of carbon atoms and from one to three heteroatoms selected from N, O and S. The heterocyclyl group may be attached at any heteroatom or carbon atom which results in the creation of a stable structure. Examples of heterocyclyl groups include, but are not limited to pyridine, pyrimidine, oxazoline, pyrrole, imidazole, morpholine, furan, indole, benzofuran, pyrazole, pyrrolidine, piperidine, and benzimidazole. "Heterocyclyl" or "heterocycle" may be substituted with one or more independent groups including, but not limited to, H, halogen, oxo, OH, $C_1$–$C_{10}$ alkyl, amino, and alkoxy.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

As used herein, the term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who has been the object of treatment, observation or experiment.

Methods are known in the art for determining therapeutically and prophylactically effective doses for the instant pharmaceutical composition. The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "prophylactically effective amount" refers to that amount of active compound or pharmaceutical agent that inhibits in a subject the onset of a disorder as being sought by a researcher, veterinarian, medical doctor or other clinician, the delaying of which disorder is mediated by the modulation of PPARγ activity.

Depending upon the biological environment (e.g., cell type, pathological condition of the host, etc.), these compounds can activate or block the actions of PPARγ. The utility of the compounds to treat disorders in glucose and lipid metabolism can be determined according to the procedures described herein. The present invention therefore provides a method of treating disorders in glucose and lipid metabolism in a subject in need thereof which comprises administering any of the compounds as defined herein in a quantity effective to such disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier. The pharmaceutical composition may contain between about 0.1 mg and 1000 mg, preferably about 100 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

To prepare the pharmaceutical compositions of this invention, one or more compounds of Formula I or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.01 mg to 30 mg/kg of body weight per day. Preferably, the range is from about 0.03 to about 15 mg/kg of body weight per day, most preferably, from about 0.05 to about 10 mg/kg of body weight per day. The compounds may be administered on a regimen of 1 to 2 times per day. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharnmaceutical diluents, e.g. water, to form a solid preformnulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The daily dosage of the products may be varied over a wide range from 1 to 1000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 30 mg/kg of body weight per day. Particularly, the range is from about 0.03 to about 15 mg/kg of body weight per day, and more particularly, from about 0.05 to about 10 mg/kg of body weight per day. The compounds may be administered on a regimen of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compound of the present invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

From Formula I it is evident that some of the compounds of the invention may have one or more asymmetric carbon atoms in their structure. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their component enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography. The scope of the present invention is intended to cover all such isomers or stereoisomers per se, as well as mixtures of cis and trans isomers, mixtures of diastereomers and racemic mixtures of enantiomers (optical isomers) as well.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known from the art.

This invention will be better understood by reference to the schemes and examples that follow, but those skilled in the art will readily appreciate that these are only illustrative of the invention as described more fully in the claims which follow thereafter.

U.S. Pat. Nos. 5,696,117 and 5,854,242, both to Frechette et al., and WO 97/17333 (Frechette et al.) describe the synthesis of compounds of Formula I wherein E is hydrogen, all of which are hereby incorporated by reference.

The compounds of Formula I can be synthesized as outlined in the following schemes and equations.

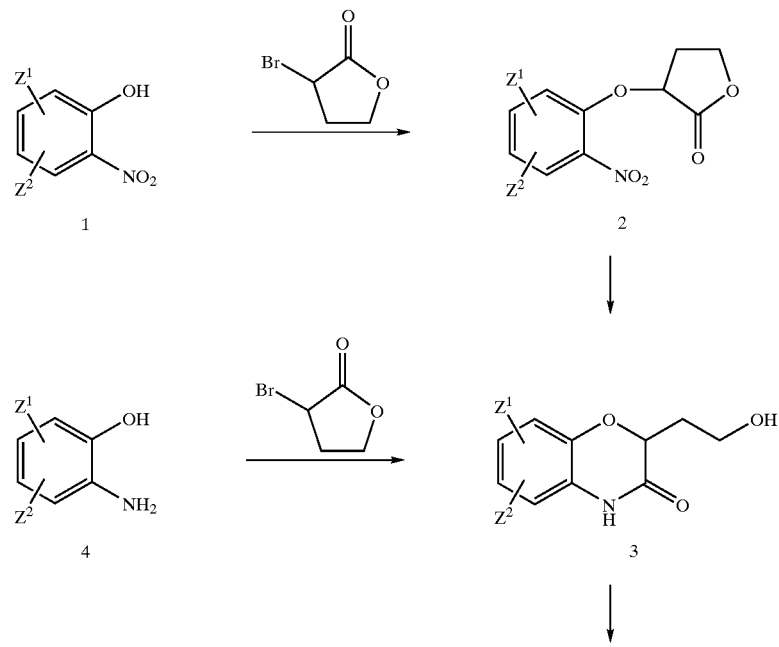

Scheme 1

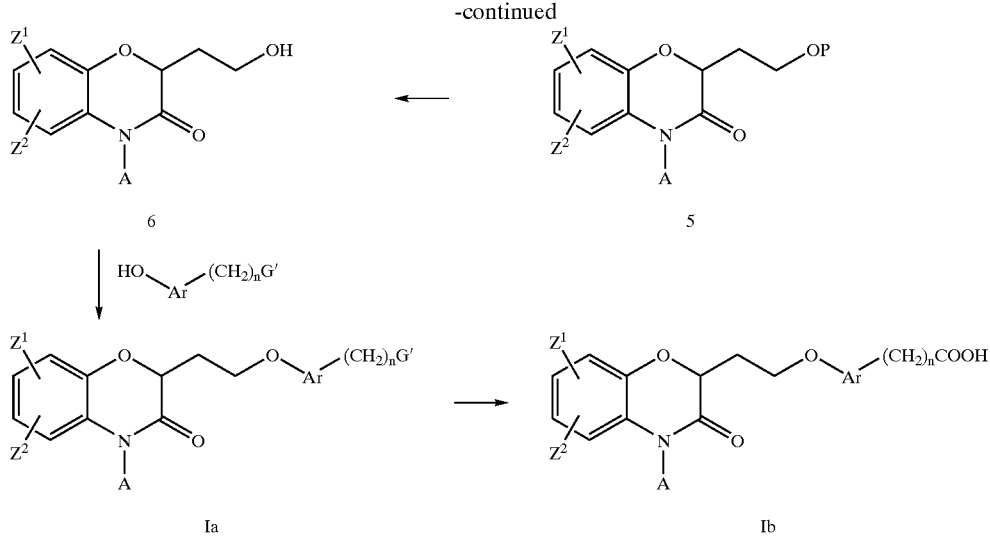

In accordance with Scheme 1, wherein Ar, $Z^1$, $Z^2$, A, G and n are as described hereinabove, the 4H-benzo[1,4] oxazin-3-ones can be made by conversion of the phenol of Formula 1, a known compound or a compound that may be prepared by known methods in the art, to the ether of Formula 2 and reduction to yield the corresponding compounds of Formula 3. Alternatively, compounds of Formula 3 can be obtained by reacting

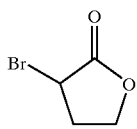

with the aminophenol of Formula 4, a known compound or a compound that may be prepared by known methods in the art. Sequential protection of the primary alcohol and substitution of the amide produces the corresponding compounds of Formula 5. Deprotection of the alcohol gives the corresponding compounds of Formula 6 that can be further converted to the alkyl aryl ether of Formula Ia by adding HO—Ar—(CH$_2$)$_n$G' (G' is G as described above other than —COOH), which are commercially available and/or may be readily prepared by known methods. Thus deprotection of the ester to the acid yields the desired product of Formula Ib. The conditions for the above steps are more fully described in U.S. Pat. Nos. 5,696,117 and 5,854,242, both to Frechette et al., and WO 97/17333 (Frechette et al.).

(eq. 1)

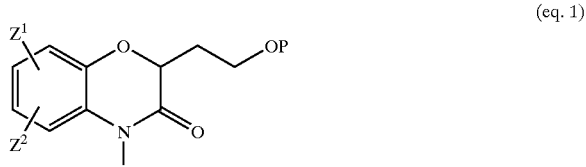

To make compounds of Formula I wherein E is $C_1$–$C_6$ alkyl, compounds of Formula 5 can be exposed to a base such as NaH, LDA, or butyllithium followed by $C_1$–$C_6$ halide (Cl, Br, or I) to yield the corresponding compounds of 9 as shown in Equation 1 wherein P represents an appropriate protecting group. Compounds of 9 can be elaborated to final products as shown in Scheme 1. This procedure also applies to the compounds of Formula I wherein X is H.

When E is

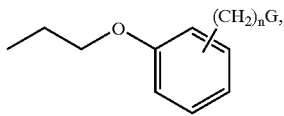

compounds of Formula I can be obtained as shown in Equation 2 and Scheme 2, wherein P and P' are appropriate protecting groups and $Z^1$, $Z^2$, A, G and n are as described hereinabove, by replacement of α-bromo-γ-butyrolactone in Scheme 1 with a reagent such as 10.

(eq. 2)

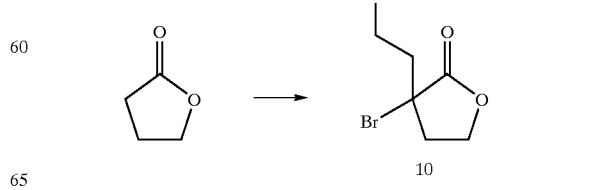

As represented by eq.2, treatment of γ-butyrolactone with a base, such as lithium diisopropylamide, and an electrophile, such as 2-(tert-butyldimethylsiloxy)ethyl bromide, then a base, such as lithium diisopropylamide, and a brominating agent, such as carbon tetrabromide, would yield the reagent 10.
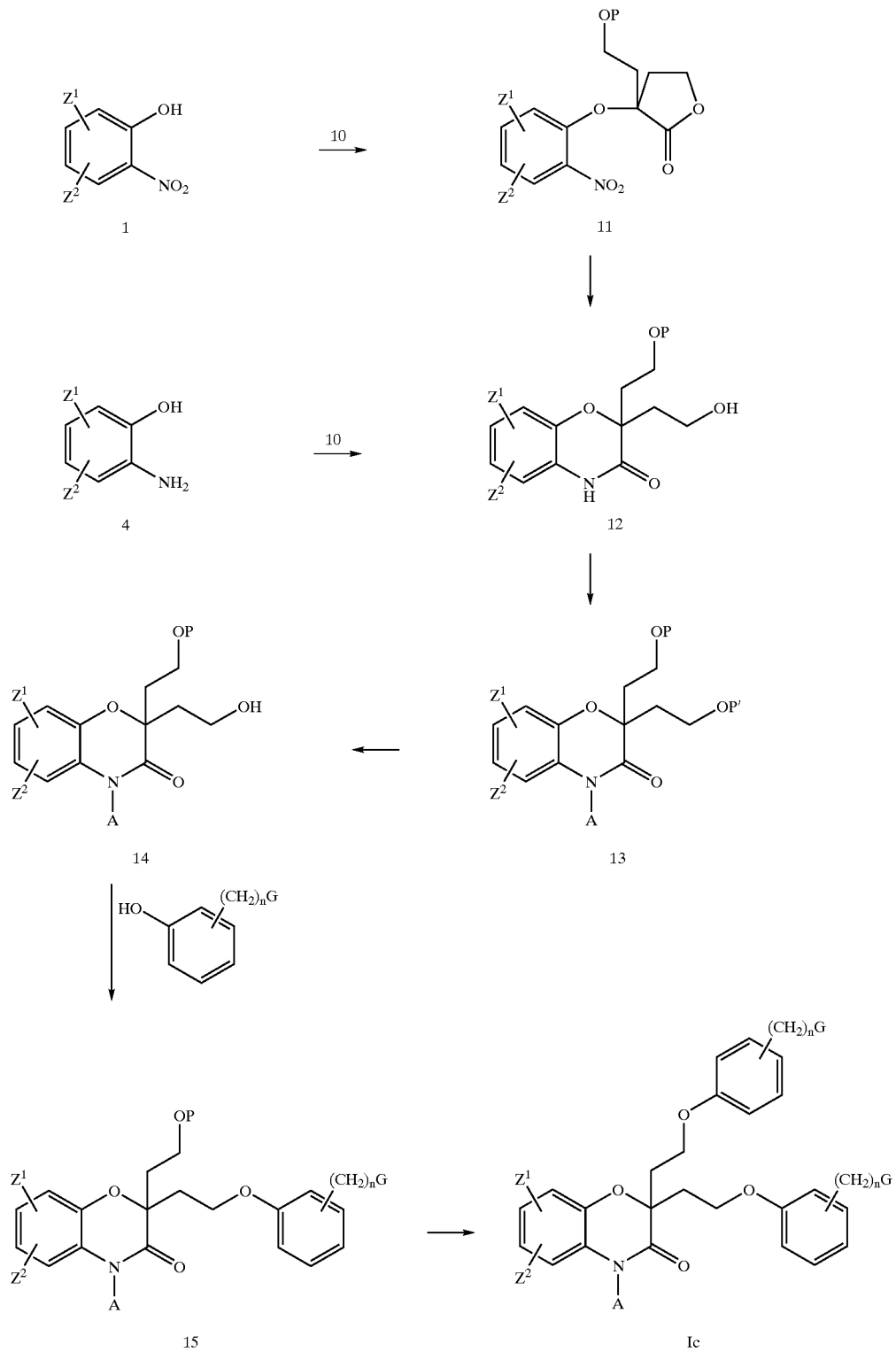
Scheme 2.

In accordance with Scheme 2, the 4H-berzo[1,4]oxanin-3-ones can be made by conversion of phenol 1 to ether 11 in the presence of the reagent 10 as described in Frechette, et al. The conversion can be carried out with a basic reagent such as an alkali metal carbonate or an alkali metal hydroxide, in a non-protic polar solvent, such as DMF (N,N-dimethylformamide) or THF, with or without heating. The resulting alkylaryl ether can be reduced to yield 12 with a reagent such as hydrogen gas or ammonium formate, and a catalyst, such as palladium or platinum, in an appropriate solvent, such as methanol, ethanol, or ethyl acetate, at an appropriate temperature preferably between room temperature and 50° C. Alternatively, compounds of Formula 12 can be obtained from aminophenol 4, by treatment of 4 with a base, such as an alkali metal hydride, in a non-protic polar solvent, such as DMF or THF, and the reagent 10, with or without heating. The primary alcohol can be protected with a reagent such as tert-butyldimethylsilyl chloride and imidazole in a non-protic polar solvent, such as DMF or THF, with or without heating. Substitution of the amide by deprotonation with a base, such as an alkali metal hydride, in a non-protic polar solvent, such as DMF or THF, and addition of an alkyl halide can produce corresponding compounds of Formula 13. Selective deprotection of the alcohol can give compounds of Formula 14. The choice of deprotection methods will vary with the choice of protecting groups, using methods such as described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The alkyl aryl ether 15 can be obtained by a reaction such as the Mitsunobu reaction as described by Frechette, et al. Deprotection of the alcohol and formation of the second alkyl aryl ether by a reaction such as the Mitunobu reaction can yield compounds of Formula Ic. These procedures also apply to the compounds of Formula I wherein X is H.

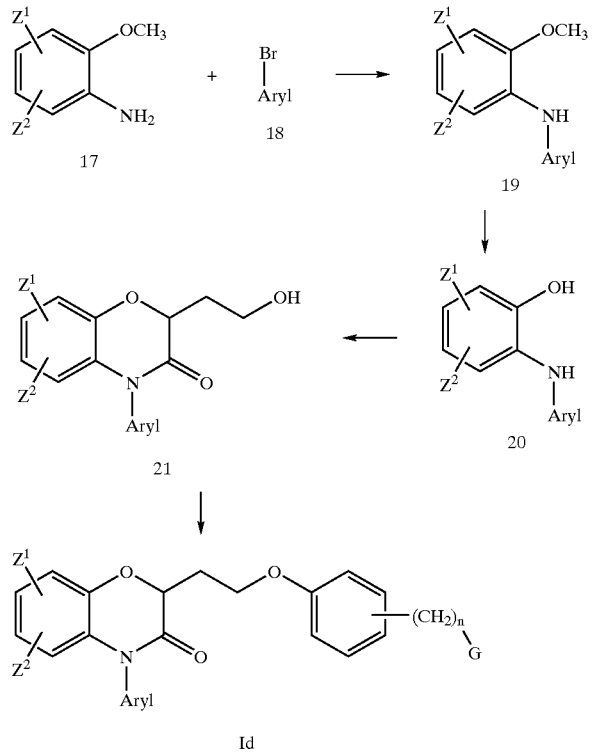

Scheme 3

In accordance with Scheme 3, the 4H-benzo[1,4]oxanin-3-ones can be made by conversion of compounds of the Formula 17 (known or made) to compounds of the Formula 19 by methods in the literature. For example, the method of Buchwald (J. Am. Chem. Soc. 1996, 118, 7215) uses a palladium catalyst and compounds of the Formula 18. Cleavage of the methyl ether can be accomplished in a number of ways such as described in T. W. Greene & P. G. M. Wuts, Protective Groups in Organic Synthesis, Third Edition, John Wiley & Sons, 1999. The choice of deprotection methods may also be found in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The resulting compounds of the Formula 20 can be utilized for the synthesis of the desired final product 22 with the method of U.S. Pat. Nos. 5,696,117 and 5,854,242, both to Frechette et al., and WO 97/17333 (Frechette et al.) outlined in Scheme 1. Thus, compounds of the Formula 20 can be treated with a base, such as an alkali metal hydride, in a non-protic polar solvent, such as DMF or THF, and 2-bromobutyrolactone, with or without heating, to provide compounds of the Formula 21. The compounds of the Formula Id can be obtained by a reaction such as the Mitsunobu reaction. These procedures also apply to the compounds of Formula I wherein X is H.

The following examples are intended to illustrate the invention but not to limit it.

EXAMPLE 1

Intermediate 1: Dihydro-3-(2-nitrophenoxy)-2-(3H)-furanone

A mixture of 2-nitrophenol (20 g, 0.14 mol) and $K_2CO_3$ (25.2 g, 0.18 mol) in 280 mL DMF was cooled to 0° C. 2-Bromobutyrolactone was added dropwise, the reaction was stirred for 45 min at 0° C., then stirred at room temperature for 3 hours (h). The mixture was poured into 2 L water containing approx. 200 g salt, and the solution was washed with 6×100 mL of 1:1 diethyl ether/ethyl acetate. The combined organics were washed with 2×100 mL sat'd aq. $K_2CO_3$, 5×100 mL water and 100 mL brine, dried ($Na_3SO_4$), and filtered. Solvent was removed in vacuo to yield the title compound as an off-white solid (21.88 g, 0.1 mol). $^1H$ ($CDCl_3$): 7.84 (d, 1H, J=7.9), 7.57 (t, 1H, J=7.5), 7.49 (d, 1H, J=7.9), 7.16 (t, 1H, J=7.5), 5.03 (t, 1H, J=7.4), 4.58 (m, 1H), 4.42 (m, 1H), 2.8–2.6 (m, 2H).

EXAMPLE 2

Intermediate 2: 2H-1,4-Benzoxazin-3(4H)-one, 2-[2-[[(1,1-dimethylethyl)dimethylailyl]oxy]ethyl]-

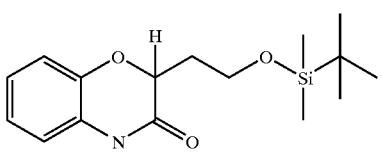

Intermediate 1 (21.88 g, 0.1 mol) was suspended in 200 mL ethanol and 200 mL EtOAc (ethyl acetate), then shaken overnight with 10% Pd/C and $H_2$ (45 psi) at room temperature. The solution was filtered through Celite and solvent was removed in vacuo. The crude product was dissolved in 200 anh. DMF, imidazole (14.1 g, 0.21 mol) was added, and the solution was cooled to 0° C. tert-Butyldimethylsilyl chloride (31.2 g, 0.21 mol) was added as a solid and the reaction was stirred overnight, under $N_2$, as the bath thawed. The reaction was poured into 1.4 L water containing approx. 200 g salt, and washed with 4×150 mL of 4:1 diethyl ether/EtOAc. The combined organics were washed with 6×100 mL water and 100 mL brine. The organics were dried ($Na_2SO_4$), filtered, and solvent was removed in vacuo. The product was isolated by silica gel chromatography with hexane/ethyl acetate. Obtain Intermediate 2 as a volatile solid (7.0 g, 0.022 mol). $^1$H (CDCl$_3$): 6.89 (m, 3H), 6.80 (m, 1H), 4.70 (m, 1H), 3.78 (m, 2H), 2.15 (m, 1H), 1.94 (m, 1H), 0.83 (s, 9H), 0.07 (s, 6H).

EXAMPLE 3

Intermediate 3 (Method A): 2H-1,4-Benzoxazin-3(-4H)-one, 2-[2-[[(1,1-dimethylethyl)dimethylsilyl]oxy]ethyl]-4-(5-oxohexyl)-

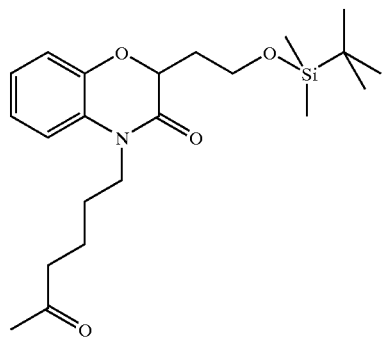

A solution of Intermediate 2 (12.8 g, 0.04 mol) in 400 mL anh. DMF, under N$_2$, was cooled to 0° C. Sodium hydride (75% dispersion in oil, 1.47 g, 0.046 mol) was added in two portions of 0.73 g with five minute intervals between additions. The solution was stirred for an additional 40 min at 0° C. 6-Chloro-2-hexanone (5.6 9, 0.04 mol) in 20 mL DMF was added dropwise, the ice bath was replaced with an oil bath, and the solution was stirred at 65° C. for 17 h. The mixture was cooled to room temperature and poured into 1.5 L water containing approx. 200 g salt. The aqueous mixture was washed with 4×125 mL of 1:1 diethyl ether/ethyl acetate. The combined organics were washed with 6×125 mL water and 125 mL brine. The organics were dried (Na$_3$SO$_4$), filtered, and solvent was removed in vacuo. The product was isolated by silica gel chromatography with hexane/ethyl acetate. Intermediate 3 was obtained as a colorless oil (13.5 g, 0.034 mol). $^1$H (CDCl$_3$) 6.92 (m, 4H), 4.63 (dd, 1H, J=9.9, 3.7), 3.85–3.69 (m, 4H), 2.41 (br t, 2H), 2.17 (m and s, 4H), 1.93 (m, 1H), 1.58 (m, 4H), 0.82 (s, 9H), 0.07 (s, 6H).

EXAMPLE 4

Intermediate 4 (Method B): 2H-1,4-Benzoxazin-3(4H)-one, 2-(2-hydroxyethyl)-4-(5-oxohexyl)-

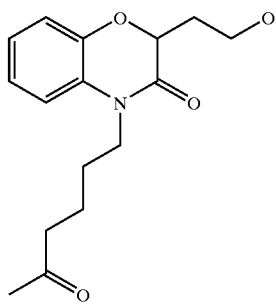

Intermediate 3 was dissolved in 40 mL methanol and 4 mL water. Methanesulfonic acid (0.5 mL) was added and the mixture was stirred at room temperature for 2 h. Solvent was removed in vacuo and the product was isolated by silica gel chromatography with hexane/ethyl acetate. Intermediate 4 was obtained as a colorless oil (7.73 g, 0.027 mol). $^1$H (CDCl$_3$) 6.77 (m, 4H), 4.51 (dd, 1H, J=8.9, 4.5), 3.70 (m, 3H), 3.55 (m, 2H), 2.29 (br t, 2H), 1.91 (m and s, 4H), 1.78 (m, 1H), 1.42 (m, 4H).

EXAMPLE 5

Compound 77 of Table 1 (Method C):
Benzeneacetic acid, 2-[2-[3,4-dihydro-3-oxo-4-(5-oxohexyl)-2H-1,4-benzoxazin-2-yl]ethoxy]-, methyl ester

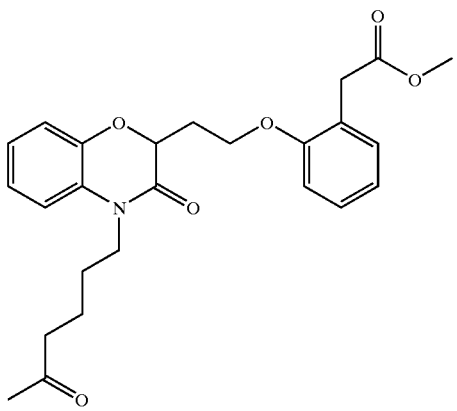

A solution of Intermediate 4 (8.75 g, 0.029 mol), methyl (2-hydroxyphenyl)acetate (7.48 g, 0.045 mol), and tributylphosphine (11.2 mL, 0.045 mol) in 500 mL anhydrous benzene, under N$_2$, was cooled to 4° C. 1,1'-(Azodicarbonyl)dipiperidine (11.34 g, 0.045 mol) was added in one portion, and the solution was stirred, with an overhead stirrer, at room temperature overnight. The organic phase was washed with 4×50 mL 2 N NaOH, 50 mL water and 50 mL brine. The organics were dried (Na$_2$SO$_4$), filtered, and solvent was removed in vacuo. The product was purified by silica gel chromatography with hexane/ethyl acetate. Compound 77 was obtained as a colorless oil (8.58 g, 0.02 mol). $^1$H (CDCl$_3$): 7.28–6.89 (m, 8H), 4.76 (dd, 1H, J=9.5, 4.0), 4.19 (m, 2H), 3.93 (br t, 2H), 3.61 and 3.60 (two singlets, 5H), 2.51 (m, 3H), 2.13 (m and s, 4H), 1.66 (m, 4H).

EXAMPLE 6

Compound 78 of Table 1 (Method D):
Benzeneacetic acid, 2-[2-[3,4-dihydro-3-oxo-4-(5-oxohexyl)-2H-1,4-benzoxazin-2-yl]ethoxy]-

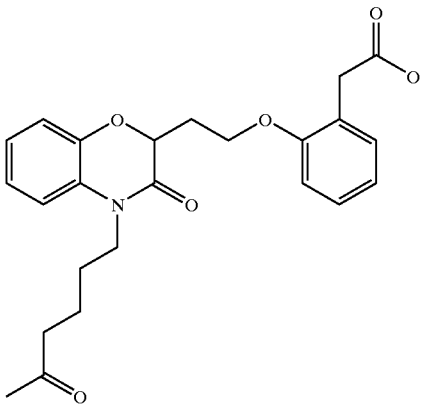

A solution of Compound 77 (0.5 g, 1.13 mol) in 10 mL THF was cooled to 0° C. LiOH (0.143 g, 3.4 mmol) in 5 mL water was added in one portion. The solution was stirred at room temperature overnight, open to air. The solution was diluted with 25 mL water and 4 mL 1N NCl. Extract with dichloromethane. The combined organics were washed with water/brine combination, dried ($Na_2SO_4$), and filtered. Compound 78 was obtained as a colorless oil (0.41 g, 0.96 mmol). $^1H$ ($CDCl_3$): 7.28–6.89 (m, 8H), 4.83 (dd, 1H, J=9.0, 3.6), 4.20 (m, 2H), 3.93 (m, 2H), 3.65 (d, 1H, J=16.0), 3.59 (d, 1H, J=16.0), 2.50 (m, 3H), 2.13 (m and s, 4H), 1.65 (m, 4H).

EXAMPLE 7

Compound 79 of Table 1: Benzeneacetic acid, 2-[2-[3,4-dihydro-4-[(5Z)-5-(hydroxyimino)hexyl]-3-oxo-2H-1,4-benzoxazin-2-yl]ethoxy]-

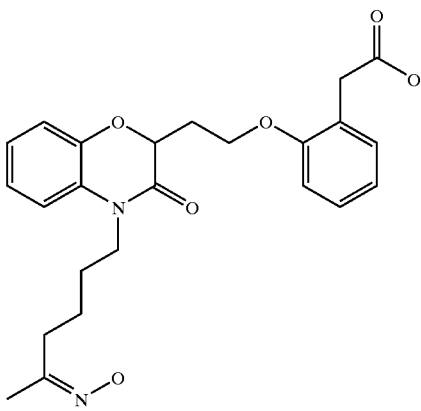

Compound 78 (4.72 g, 0.011 mol) was dissolved in 200 mL ethanol and lutidine (2.6 mL, 0.022 mol). Hydroxylamine hydrochloride (3.8 g, 0.055 mol) was added, and the reaction was stirred at room temperature for 2 hours. Solvent was removed, the residue was taken up in ethyl acetate and water, then further washed with 0.1 N HCl and water. The organics were dried ($Na_3SO_4$), filtered, and solvent was removed. Compound 79 was obtained as a white solid. $^1H$ ($CDCl_3$): 7.25 (m, 2H), 6.95 (m, 6H), 4.87 (dd, 1H, J=9.5, 3.6), 4.27 (m, 2H), 4.15 (m, 1H), 3.91 (m, 1H), 3.65 (d, 1H, J=15.3), 3.59 (d, 1H, J=15.3), 2.50 (m, 1H), 2.4–2.1 (m, 3H), 1.9 (s, major isomer, approx. 3H) and 1.82 (s, minor isomer) 1.7–1.4 (m, 4H).

EXAMPLE 8

Compound 81 of Table 1: Benzeneacetic acid, 2-[2-[3,4-dihydro-4-(5-hydroxyhexyl)-3-oxo-2H-1,4-benzoxazin-2-yl]ethoxy]-, methyl ester

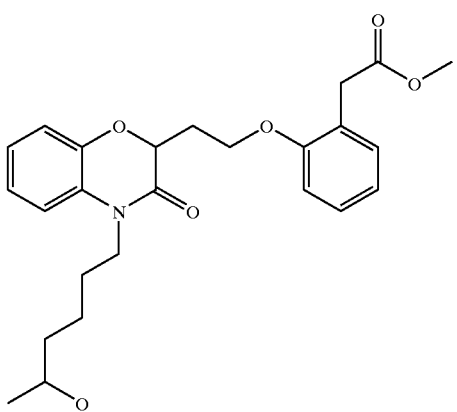

A slurry of Compound 78 (0.2 g, 0.00046 mol) in 10 mL ethanol was treated with sodium borohydride (0.012 mg, 0.00031 mol), then stirred for 1 hour at room temperature. The reaction was diluted with water and extracted with ethyl acetate. The organics were dried ($Na_2SO_4$), filtered, and solvent was evaporated. Compound 81 was obtained as a colorless oil (0.052 g, 0.00012 mol). $^1H$ ($CDCl_3$): 7.25 (m, 2H), 6.95 (m, 6H), 4.76 (dd, 1H, J=9.4, 3.9), 4.23 (m, 2H), 3.94 (t, 2H, J=7.5), 3.80 (m, 1H), 3.61 and 3.60 (two singlets, 5H), 2.49 (m, 1H), 2.23 (m, 1H), 1.70 (m, 2H), 1.47 (m, 4H), 1.19 (d, 3H, J=6.0).

EXAMPLE 9

Compound 82 of Table 1: Benzeneacetic acid, 2-[2-[3,4-dihydro-4-(5-hydroxyhexyl)-3-oxo-2H-1,4-benzoxazin-2-yl]ethoxy]-

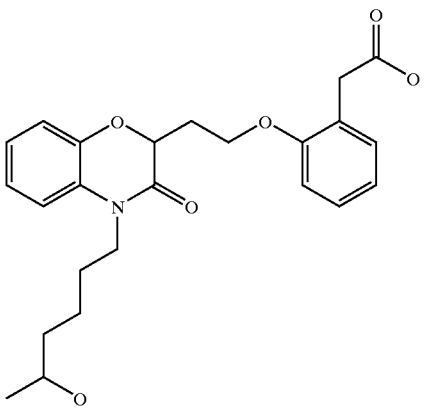

Prepared from Compound 81 (0.052 g, 0.00012 mol) in a manner analogous to Method D. Compound 82 was obtained as a colorless oil (0.040 g, 0.0001 mol). $^1H$ ($CDCl_3$): 7.25 (m, 2H), 6.95 (m, 6H), 4.87 (br d, 1H), 4.4–3.8 (m, 6H), 3.59 (s, 2H), 2.49 (m, 1H), 2.20 (m, 1H), 1.71 (m, 2H), 1.50 (m, 4H), 1.19 (m, 3H).

EXAMPLE 10

Intermediate 5: 1-Bromo-6-fluorohexane (Diethylamino)sulfur trifluoride (4.0 mL, 0.031 mol) was cooled to 0° C., and 6-bromohexan-1-ol (2.0 mL, 0.015 mol) was added dropwise. The mixture was heated to 35° C. for 4 h, then carefully poured into ice water. The aqueous phase was washed with methylene chloride. The organic phase was dried ($Na_3SO_4$), filtered, and solvent was removed in vacuo. 1-Bromo-6-fluorohexane was purified by silica gel chromtography with hexane/methylene chloride (2.1 g, 0.012 mol). $^1H$ ($CDCl_3$): 4.45 (dt, 2H, J=47.3, 6.0), 3.42 (t, 2H, J=6.6), 1.9–1.1 (m, 8H).

EXAMPLE 11

Intermediate 6: 2H-1,4-Benzoxazin-3(4H)-one, 2-[2-[[(1,1-dimethylethyl)dimethylsilyl]oxy]ethyl]-4-(6-fluorohexyl)-

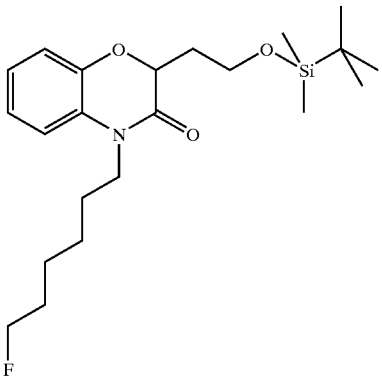

Prepared from Intermdiate 2 (3.3 g, 0.011 mol) and 1-bromo-6-fluorohexane (2.0 g, 0.011 mol) in a manner analogous to Method A. Intermediate 6 was obtained as a colorless oil (2.9 g, 0.007 mol). MS (MH$^+$): m/z=410.

EXAMPLE 12

Intermediate 7: 2H-1,4-Benzoxazin-3(4H)-one, 4-(6-fluorohexyl)-2-(2-hydroxyethyl)-

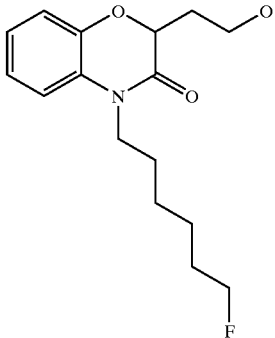

Prepared from Intermediate 6 (2.9 g, 0.007 mol) in a manner analogous to Method B. Intermediate 7 was obtained as a colorless oil (1.9 g, 0.006 mol). $^1$H (CDCl$_3$): 7.02 (m, 4H), 4.69 (t, 1H, J=7.0), 4.44 (dt, 2H, J=47.3, 6.0), 3.88 (m, 4H), 2.37 (t, 1H, J=5.8), 2.21 (m, 2H), 1.68 (m, 4H), 1.46 (m, 4H).

EXAMPLE 13

Compound 90 of Table 1: Benzeneacetic acid, 2-[2-[4-(6-fluorohexyl)-3,4-dihydro-3-oxo-2H-1,4-benzoxazin-2-yl]ethoxy]-, methyl ester

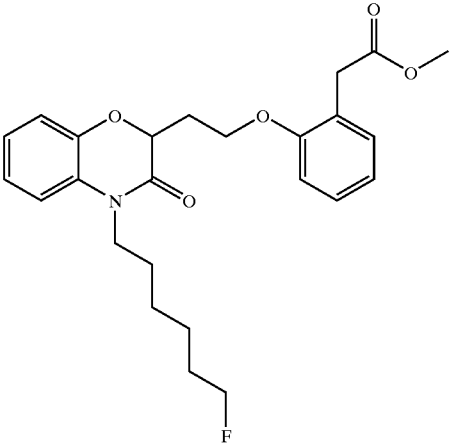

Prepared from Intermediate 7 (1.8 g, 0.006 mol) in a manner analogous to Method C. Compound 90 was obtained as a colorless oil (2.2 g, 0.005 mol). $^1$H (CDCl$_3$): 7.28–6.89 (m, 8H), 4.76 (dd, 1H, J=9.5, 4.0), 4.44 (dt, 2H, J=47.3, 6.0), 4.19 (m, 2H), 3.93 (br t, 2H), 3.61 and 3.60 (two singlets, 5H), 2.50 (m, 3H), 2.22 (m, 1H), 1.68 (m, 4H), 1.57 (m, 4H).

EXAMPLE 14

Compound 91 of Table 1 (Method E): Benzeneacetic acid, 2-[2-[4-(6-fluorohexyl)-3,4-dihydro-3-oxo-2H-1,4-benzoxazin-2-yl]ethoxy]-

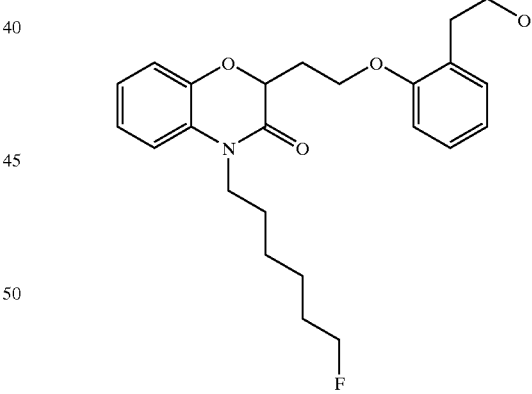

A solution of Compound 90 (2.1 g, 0.005 mol) in 25 mL methanol and 5 mL 2 N NaOH was heated to 55° C. The solution was stirred for two hours, open to air. The solution was diluted with 25 mL water and 2 mL 6N HCl. Extract with dichloromethane. The combined organics were washed with water/brine combination, dried (Na$_2$SO$_4$), and filtered. Compound 91 was obtained as a colorless oil, then crystallized from pentane/diethyl ether (1.8 g, 0.004 mmol). $^1$H (CDCl$_3$): 7.28–6.89 (m, 8H), 4.86 (dd, 1H, J=9.1, 3.6), 4.20 (m, 2H), 4.44 (dt, 2H, J=47.2, 6.1), 4.21 (m, 2H), 3.93 (br t, 2H), 3.66 (d, 1H, J=16.0) and 3.59 (d, 1H, J=16.0), 2.40 (m, 1H), 2.23 (m, 1H), 1.68 (m, 4H), 1.45 (m, 4H).

EXAMPLE 15

Intermediate 8: 2H-1,4-Benzoxazin-3(4H)-one, 2-[2-[[(1,1-dimethylethyl)dimethylsilyl]oxy]ethyl]-4-hexyl-

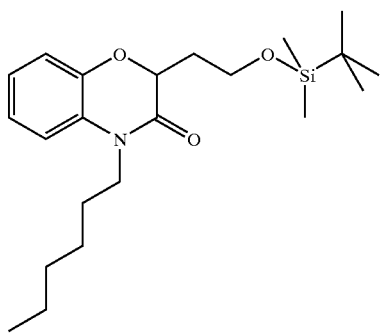

Prepared from Intermediate 1(15.00 g, 0.049 mol) and 1-iodohexane (7.2 mL, 0.049 mol) in a manner analogous to Method A. Intermediate 8 was obtained as a colorless oil (18.03 g, 0.046 mol). $^1$H (CDCl$_3$): 7.0 (m, 4H), 4.72 (dd, 1H, J=10.0, 3.6), 3.95–3.75 (m, 4H), 2.17 (m, 1H), 1.93 (m, 1H), 1.33 (m, 6H), 0.89 (s, 12H), 0.07 (s, 6H).

EXAMPLE 16

Intermediate 9: 2H-1,4-Benzoxazin-3(4H)-one, 4-hexyl-2-(2-hydroxyethyl)-

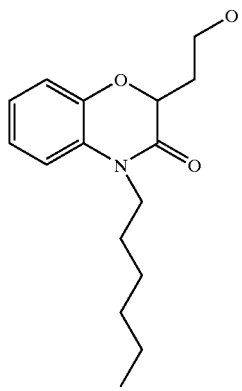

Prepared from Intermediate 8 (18.3 g, 0.046 mol) in a manner analogous to Method B. Intermediate 9 was obtained as a colorless oil (11.16 g, 0.04 mol) ) $^1$H (CDCl$_3$) 7.01 (m, 4H), 4.69 (t, 1H, J=7.0), 3.88 (m, 4H), 2.44 (t, 1H, J=5.8), 2.20 (m, 2H), 1.65 (m, 2H), 1.33 (m, 6H), 0.89 (br t, 3H).

EXAMPLE 17

Compound 14 of Table 1: Phosphonic acid, [[2-[2-(4-hexyl-3,4-dihydro-3-oxo-2H-1,4-benzoxazin-2-yl)ethoxy]phenyl]methyl]-, diethyl ester

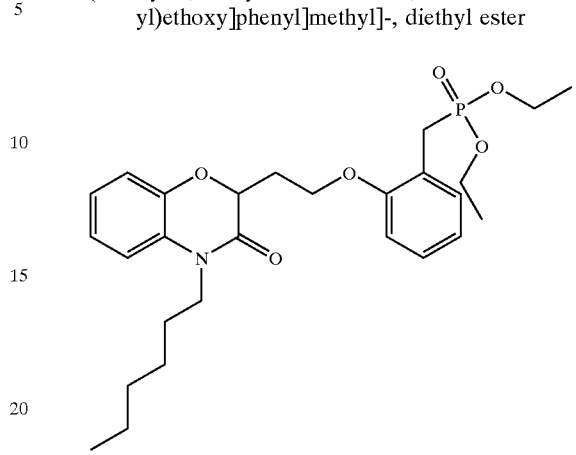

Prepared from Intermediate 9 (1.13 g, 0.004 mol) and 2-(hydroxybenzyl)-phosphonic acid diethyl ester (*J. Org. Chem.* 1983, 48, 4768; 1.0 g, 0.04 mol) in a manner analogous to Method C. Compound 14 was obtained as a colorless oil (1.6 g, 0.003 mol). $^1$H (CDCl$_3$): 7.4–6.7 (m, 8H), 4.81 (dd, 1H, J=9.2, 4), 4.4–3.9 (m, 8H), 3.24 (m, 2H), 2.55 (m, 1H), 2.27 (m, 1H), 1.64 (m, 2H), 1.5–1.2 (m, 14H), 0.89 (br t, 3H).

EXAMPLE 18

Compound 15 of Table 1: Phosphonic acid, [[2-[2-(4-hexyl-3,4-dihydro-3-oxo-2H-1,4-benzoxazin-2-yl)ethoxy]phenyl]methyl]-

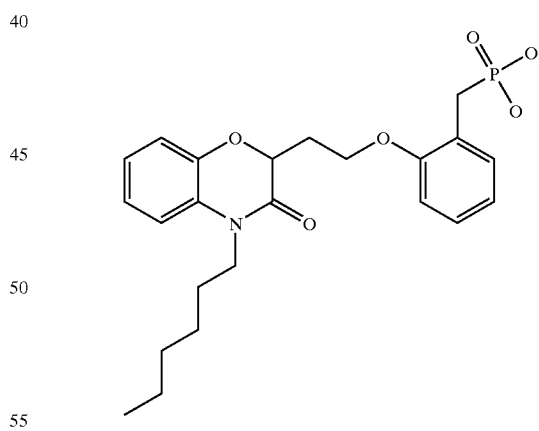

A solution of Compound 14 (0.5 g, 0.001 mol) in 25 mL 6N HCl was cooled to reflux overnight, open to air. Extract with 4×20 mL dichloromethane. The combined organics were washed with water and brine, dried (Na$_3$SO$_4$) and filtered. Solvent was removed in vacuo. Compound 15, contaminated with the half ester, was obtained as a colorless oil. (0.25 g, 0.0005 mol). $^1$H (CDCl$_3$): 7.4–6.7 (m, 8H), 4.90 (m, 1H), 4.3–3.8 (m, 6H), 3.19 (m, 2H), 2.53 (m, 1H), 2.22 (m, 1H), 1.64 (m, 2H), 1.5–1.2 (m, 8H), 1.14 (t, from the half ester), 0.89 (br t, 3H). MS (M$^-$): m/z=474.

EXAMPLE 19

Intermediate 10: Benzeneacetic acid, 2-[2-(4-hexyl-3,4-dihydro-3-oxo-2H-1,4-benzoxazin-2-yl)ethoxy]-, methyl ester

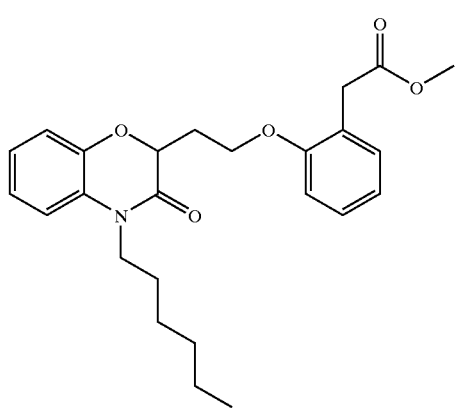

Prepared from Intermediate 9 (11.16 g, 0.04 mol) in a manner analogous to Method C. Intermediate 10 was obtained as a colorless oil (9.7 g, 0.023 mol). $^1$H (CDCl$_3$): 7.28–6.89 (m, 8H), 4.76 (dd, 1H, J=9.4, 4), 4.28–4.21 (m, 2H), 3.92 (t, 2H, J=7.7), 3.60 (two singlets, 5H), 2.49 (m, 1H), 2.23 (m, 1H), 1.66 (m, 2H), 1.34 (m, 6H), 0.89 (br t, 3H).

EXAMPLE 20

Intermediate 11: Benzeneacetic acid, 2-[2-(4-hexyl-3,4-dihydro-3-oxo-2H-1,4-benzoxazin-2-yl)ethoxyl]-

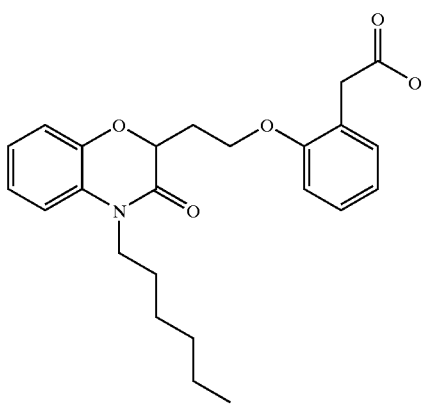

Prepared from Intermediate 10 (26.5 g, 0.062 mol) in a manner analogous to Method D. Intermediate 11 was obtained by crystallization from pentane and diethyl ether (21.5 g, 0.052 mol). m.p. 80.0–81.5° C. $^1$H (CDCl$_3$): 7.28–6.89 (m, 8H), 4.88 (dd, 1H, J=9.0, 3.5), 4.20 (m, 2H), 3.91 (t, 2H, J=7.8), 3.67 (d, 1H, J=16.0), 3.60 (d, 1H, J=16.0), 2.43 (m, 1H), 2.23 (m, 1H), 1.65 (m, 2H), 1.33 (m, 6H), 0.88 (br t, 3H).

EXAMPLE 21

Compound 11 of Table 1 (Method F): Benzeneacetamide, 2-[2-(4-hexyl-3,4-dihydro-3-oxo-2H-1,4-benzoxazin-2-yl)ethoxy]-

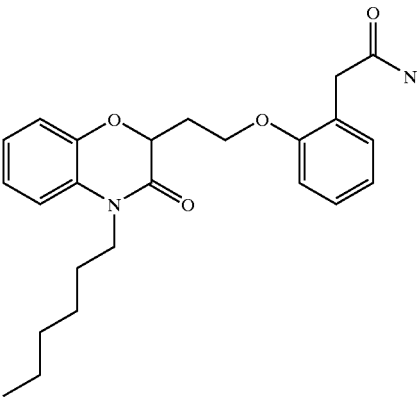

Intermediate 11 (0.1 g, 0.00024 mol) was dissolved in 10 mL CH$_2$Cl$_2$ at room temperature. Carbonyl diimidazole (0.079 g, 0.0005 mol) was added and the stirred for 2 hours. Excess ammonia gas was added and the solution was stirred at room temperature for 30 minutes. The product was purified by silica gel chromatography with hexane/ethyl acetate. Compound 11 was obtained as a white solid (0.068 g, 0.00017 mol). 1H (CDCl$_3$): 7.28–6.89 (m, 8H), 4.78 (dd, 1H, J=8.2, 4.4), 4.25 (m, 2H), 3.91 (t, 2H, J=7.1), 3.58 (d, 1H, J=14.8), 3.52 (d, 1H, J=14.8), 2.50 (m, 1H), 2.37 (m, 1H), 1.65 (m, 2H), 1.33 (m, 6H), 0.89 (br t, 3H).

EXAMPLE 22

Compound 12 of Table 1: Benzeneacetic acid, 2-[2-(4-hexyl-3,4-dihydro-3-oxo-2H-1,4-benzoxazin-2-yl)ethoxy]-a-oxo-, methyl ester

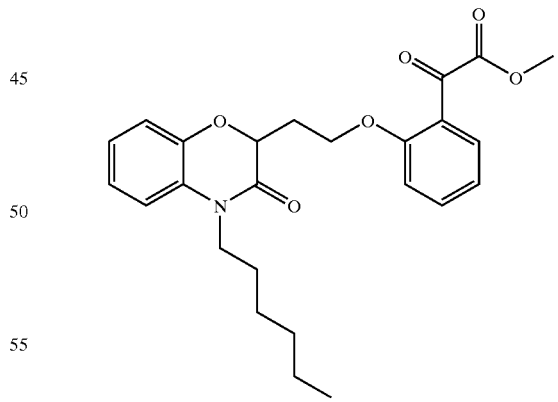

Prepared from Intermediate 9 (0.61 g, 0.0022 mol) and 2-hydroxy-α-oxo-bezeneacetic acid, methyl ester (0.4 g, 0.0022 mol). Compound 12 was obtained as a colorless oil (0.48 g, 0.0011 mol). $^1$H (CDCl$_3$): 7.88 (d, 1H, J=7.4), 7.58 (t, 1H, J=6.5), 6.99 (m, 6H), 4.65 (dd, 1H, J=9.6, 3.9), 4.57 (t, 2H, J=7.4), 4.32 (m, 1H), 3.87 (s and m, 4H), 2.49 (m, 1H), 2.24 (m, 1H), 1.62 (m, 2H), 1.32 (m, 6H), 0.88 (br t, 3H).

EXAMPLE 23

Compound 13 of Table 1: Benzeneacetic acid, 2-[2-(4-hexyl-3,4-dihydro-3-oxo-2H-1,4-benzoxazin-2-yl)ethoxy]-a-oxo-

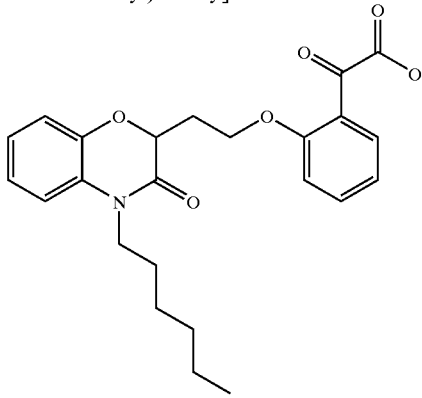

Prepared from Compound 12 (0.2 g, 0.0005 mol) in a manner analogous to Method E. Compound 13 was obtained as a white solid from acetone (0.038 g, 0.0001 mol).

$^1$H (CD$_3$OD): 7.83 (d, 1H, J=7.9), 7.55 (t, 1H, J=6.9), 7.02 (m, 6H), 5.00 (dd, 1H, J=9.7, 3.9), 4.34 (m, 1H), 4.25 (m, 1H), 3.97 (m, 2H), 2.49 (m, 1H), 2.20 (m, 1H), 1.64 (m, 2H), 1.34 (m, 6H), 0.90 (br t, 3H).

EXAMPLE 24

Intermediate 12: Benzyl 6-bromohexanoate

6-Bromohexanoic acid (10.0 g, 0.051 mol), benzyl alcohol (6.1 g, 0.056 mol) and DMAP (dimethylaminopyridine, 0.63 g, 0.005 mol) were dissolved in 100 mL CH$_2$Cl$_2$, then cooled to 0° C. 1-(3-Dimethylaminopropyl)-3-ethylcarbodiimide hydrochloride (EDC, 10.8 g, 0.056 mol) was added and the reaction stirred overnight at room temperature. The organics were diluted with CH$_2$Cl$_2$ and washed with water, aq. NaHCO$_3$, and brine. The organic phase was dried (Na$_2$SO$_4$), filtered, and solvent was removed. Intermediate 12 was obtained as a colorless oil (11.6 g, 0.04 mol). MS(MH$^+$): m/z=286.

EXAMPLE 25

Intermediate 13: 2H-1,4-Benzoxazine-4-hexanoic acid, 2-[2-[[(1,1-dimethylethyl)dimethylsilyl]oxy]ethyl]-3,4-dihydro-3-oxo-, phenylmethyl ester

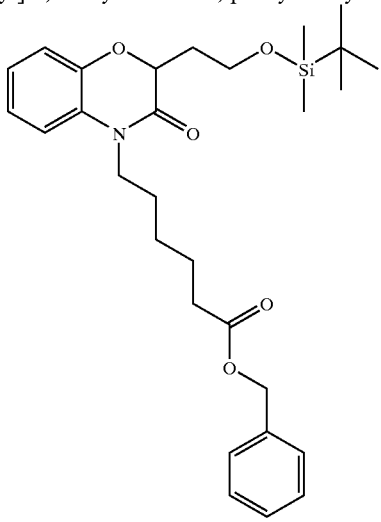

Prepared from Intermediate 2 (7.5 g, 0.024 mol) and Intermediate 12 (7.0 g, 0.025 mol) in a manner analogous to Method A. Intermediate 13 was obtained as a colorless oil (13 g, 0.024 mol). MS(MH$^+$): m/z=512.

EXAMPLE 26

Intermediate 14 (Method G): 2H-1,4-Benzoxazine-4-hexanoic acid, 3,4-dihydro-2-(2-hydroxyethyl)-3-oxo-, phenylmethyl ester

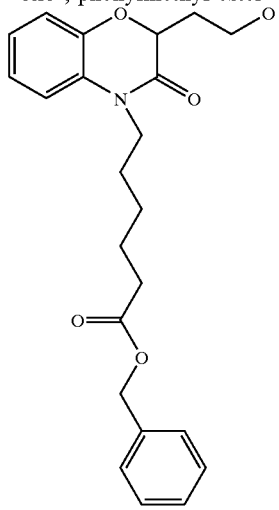

Intermediate 13 (13.7 g, 0.027 mol) was dissolved in 50 mL THF (tetrahydrofuran). Tetrabutylammonium fluoride (1.0 M in THF, 15.5 mL) was added and stirring continued under N$_2$ for 5 hours. Solvent was removed, the residue was taken up in ether and washed with water. The product was isolated by silica gel chromatography with hexane and ethyl actate. Intermediate 14 was obtained as a colorless oil (10 g, 0.025 mmol). $^1$H (CDCl$_3$): 7.34 (m, 5H), 7.00 (m, 4H), 5.10 (s, 2H), 4.68 (t, 1H, J=5.6), 3.87 (m, 4H), 2.36 (t, 2H, J=7.3), 2.19 (m, 2H), 1.67 (m, 4H), 1.37 (m, 2H).

EXAMPLE 27

Compound 99 of Table 1: 2H-1,4-Benzoxazine-4-hexanoic acid, 3,4-dihydro-2-[2-[2-(2-methoxy-2-oxoethyl)phenoxy]ethyl]-3-oxo-, phenylmethyl ester

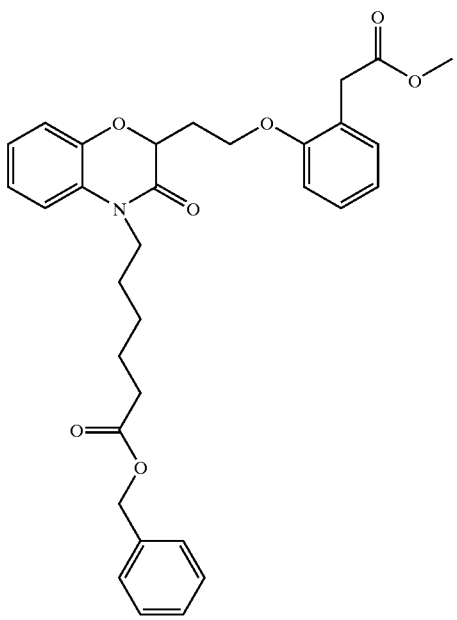

Prepared from Intermediate 14 (5.0 g, 0.013 mol) in a manner analogous to Method C. Compound 99 was obtained as a colorless oil (5.0 g, 0.009mol). $^1$H (CDCl$_3$) 7.4–6.8 (m, 13H), 5.11 (s, 2H), 4.75 (dd, 1H, J=9.5, 3.9), 4.20 (m, 2H), 3.91 (t, 2H, J=7.4), 3.61 and 3.59 (two singlets, 5H), 2.51 (m, 1H), 2.37 (t, 2H, J=7.4), 2.22 (m, 1H), 1.73 (m, 4H), 1.41 (m, 2H).

EXAMPLE 28

Compound 100 of Table 1: 2H-1,4-Benzoxazine-4-hexanoic acid, 3,4-dihydro-2-[2-[2-(2-methoxy-2-oxoethyl)phenoxy]ethyl]-3-oxo-

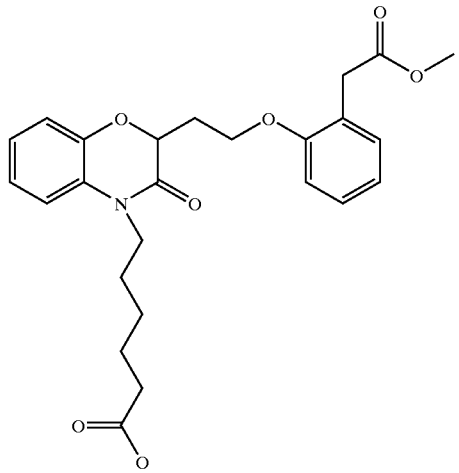

Compound 99 (5.0 g, 0.009 mol) was dissolved in 50 mL ethanol. The solution was exposed to 10% Pd/C and 50 psi H2 for 4 hours. The solution was filtered through Celite and evaporated. Compound 100 was obtained as a colorless oil (3.7 g, 0.008 mol). $^1$H (CDCl$_3$): 7.4–6.8 (m, 8H), 4.77 (dd, 1H, J=9.5, 3.7), 4.18 (m, 2H), 3.93 (t, 2H, J=7.1), 3.62 and 3.60 (two singlets, 5H), 2.48 (m, 1H), 2.34 (m, 2H), 2.22 (m, 1H), 1.68 (m, 4H), 1.43 (m, 2H).

EXAMPLE 29

Compound 101 of Table 1: 2H-1,4-Benzoxazine-4-hexanoic acid, 2-[2-[2-(carboxymethyl)phenoxy]ethyl]-3,4-dihydro-3-oxo-

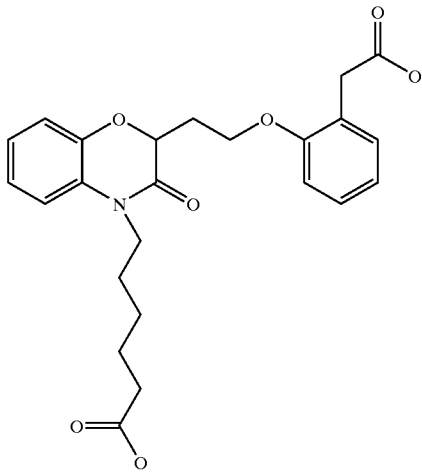

Prepared from Compound 100 (0.4 g, 0.0009 mol) in a manner analogous to Method E. Obtain Compound 101 as a white solid (0.25 g, 0.0006 mol). $^1$H (CD$_3$OD): 7.3–6.8 (m, 8H), 4.83 (m, 1H), 4.19 (m, 2H), 3.97 (m, 2H), 3.58 (m, 2H), 2.5–2.1 (m, 4H), 1.64 (m, 4H), 1.40 (m, 2H).

EXAMPLE 30

Compound 97 of Table 1: Benzeneacetic acid, 2-[2-[4-(6-amino-6-oxohexyl)-3,4-dihydro-3-oxo-2H-1,4-benzoxazin-2-yl]ethoxy]-, methyl ester

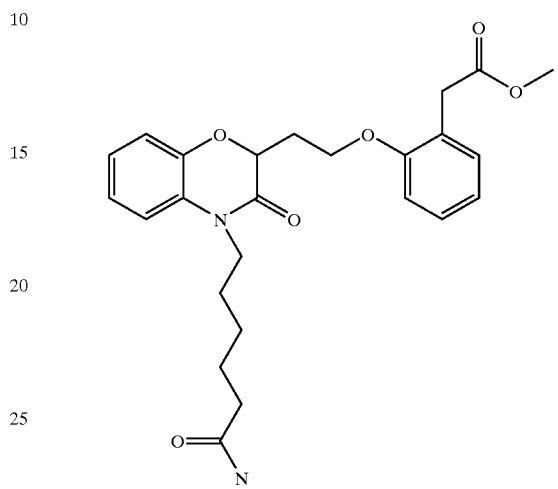

Prepared from Compound 100 (0.4 g, 0.0009 mol) in a manner analogous to Method F. Obtain Compound 97 as a solid (0.3 g, 0.0007 mol). $^1$H (CDCl$_3$): 7.4–6.8 (m, 8H), 4.76 (dd, 1H, J=9.3, 4.1), 4.23 (m, 2H), 3.94 (t, 2H, J=7.2), 3.62 and 3.59 (two singlets, 5H), 2.50 (m, 1H), 2.25 (m, 3H), 1.70 (m, 4H), 1.42 (m, 2H).

EXAMPLE 31

Compound 98 of Table 1: Benzeneacetic acid, 2-[2-[4-(6-amino-6-oxohexyl)-3,4-dihydro-3-oxo-2H-1,4-benzoxazin-2-yl]ethoxy]-

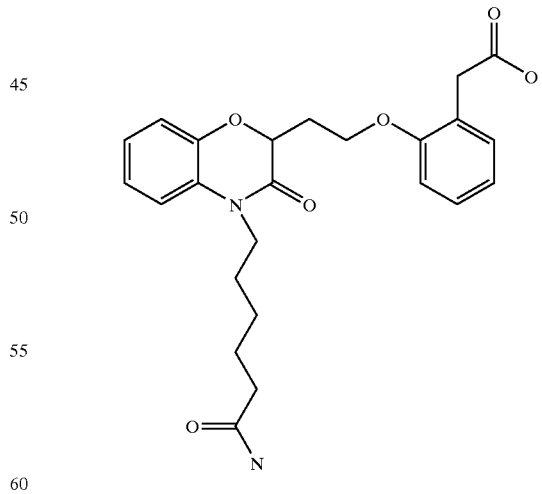

Prepared from Compound 97 (0.3 g, 0.0007 mol) in a manner analogous to Method D. Obtain Compound 98 as a white solid (0.24 g, 0.0005 mol). $^1$H (DMSO): 7.3–6.8 (m, 8H), 4.79 (dd, 1H, J=9.2, 4.0), 4.15 (m, 2H), 3.90 (t, 2H, J=7.2), 3.50 (s, 2H), 2.27 (m, 1H), 2.02 (m, 3H), 1.50 (m, 4H), 1.28 (m, 2H).

EXAMPLE 32

Intermediate 15: 2H-1,4-Benzoxazin-3(4H)-one, 2-[2-[[(1,1-dimethylethyl)dimethylsilyl]oxy]ethyl]-4-[[3-(trifluoromethyl)phenyl]methyl]-

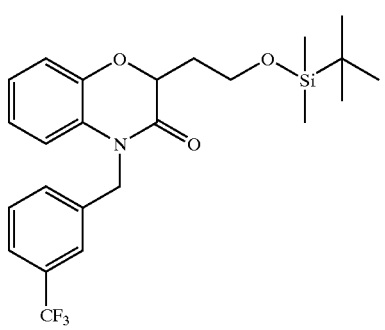

Prepared from Intermediate 2 (1.38 g, 0.005 mol) and 3-trifluoromethylbenzyl bromide (0.7 mL, 0.005 mol) in a manner analogous to Method A. Intermediate 15 was obtained as a colorless oil (1.97 g, 0.004 mmol). $^1$H (CDCl$_3$): 7.6–7.3 (m, 4H), 6.9–6.8 (m, 3H), 6.70 (d, 1H, J=8 Hz), 5.10 (s, 2H), 4.79 (dd, 1H, J=9.8, 3.7), 3.82 (m, 2H), 2.20 (m, 1H), 1.93 (m, 1H), 0.82 (s, 9H), 0.0 (s, 6H).

EXAMPLE 33

Intermediate 16: 2H-1,4-Benzoxazin-3(4H)-one, 2-(2-hydroxyethyl)-4-[[3-(trifluoromethyl)phenyl]methyl]-

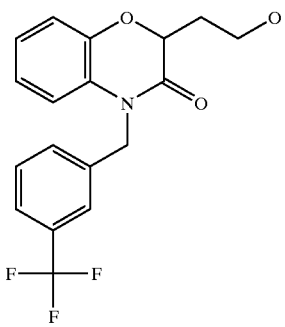

Prepared from intermediate 15 (1.97 g, 0.004 mol) in a manner analogous to Method G. Intermediate 16 was obtained as a colorless oil (1.14 g, 0.003 mmol). $^1$H (CDCl$_3$) 7.6–7.3 (m, 4H), 6.9–6.8 (m, 3H), 6.70 (d, 1H, J=8 Hz), 5.20 (s, 2H), 4.88 (t, 1H, J=5.5), 3.82 (t, 2H, J=5.7), 2.4–2.1 (m, 3H).

EXAMPLE 34

Compound 9 of Table 1: Benzoic acid, 2-[2-[3,4-dihydro-3-oxo-4-[[3-(trifluoromethyl)phenyl]methyl]-2H-1,4-benzoxazin-2-yl]ethoxy]-, methyl ester

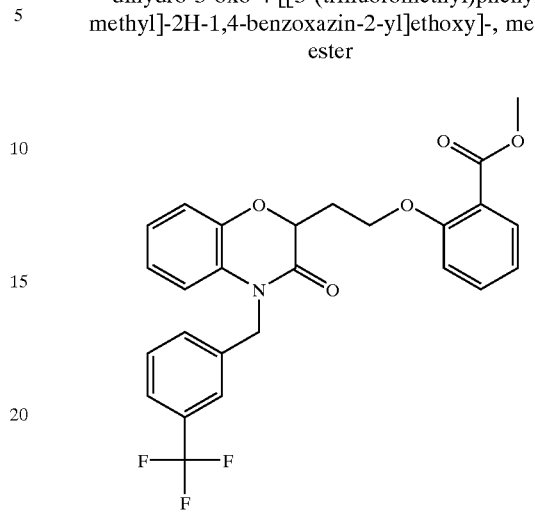

Prepared from Intermediate 16 (0.183 g, 0.0005 mol) and methyl salicylate (0.119 g, 0.0008 mol) in a manner analogous to Method C. Compound 9 was obtained as a colorless oil (0.22 g, 0.0004 mmol). $^1$H (CDCl$_3$) 7.81 (dd, 1H, J=7.7, 1.8), 7.6–7.3 (m, 5H), 7.0–6.9 (m, 5H), 6.81 (d, 1H, J=7.4 Hz), 5.21 (s, 2H), 5.08 (dd, 1H, J=9.5, 4.0), 4.33 (m, 2H), 3.84 (s, 3H) 2.65 (m, 1H), 2.36 (m, 1H)

EXAMPLE 35

Compound 26 of Table 1: Benzoic acid, 2-[2-[3,4-dihydro-3-oxo-4-[[3-(trifluoromethyl)phenyl]methyl]-2H-1,4-benzoxazin-2-yl]ethoxy]-, monosodium salt

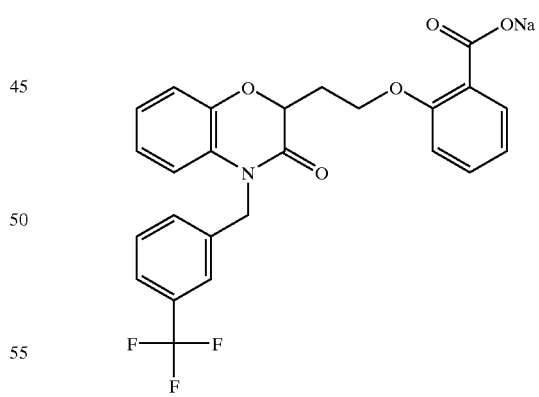

Prepared from Compound 9 (0.182 g, 0.0004 mol) in a mariner analogous to Method E, but after dilution of the completed reaction, product was isolated without addition of 6N HCl. The solid was filtered to yield Compound 26 as a sodium salt (0.141 g, 0.0003 mol). $^1$H (DMSO): 7.81 (dd, 1H, J=7.7, 1.8), 7.6–7.3 (m, 5H), 7.0–6.9 (m, 5H), 6.81 (d, 1H, J=7.4 Hz), 5.21 (s, 2H), 5.08 (dd, 1H, J=9.5, 4.0), 4.33 (m, 2H), 3.84 (s, 3H) 2.65 (m, 1H), 2.36 (m, 1H).

EXAMPLE 36

Compound 127 of Table 2: Benzeneacetic acid, 2-[2-(4-hexyl-3,4-dihydro-2-methyl-3-oxo-2H-1,4-benzoxazin-2-yl)ethoxy]-, methyl ester

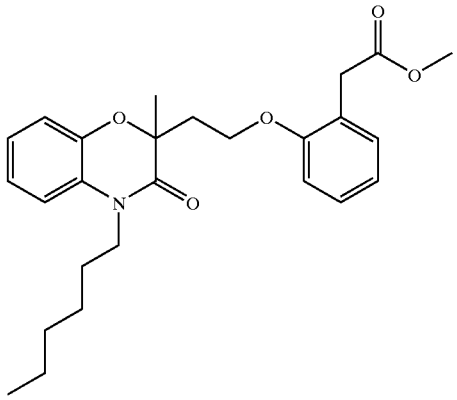

Intermediate 11 (0.26 g, 0.0006 mol) was dissolved in 10 ml THF and cooled to 0° C. Sodium hexamethyldisilazide (1.8 mL, 1.0 M) was added, then the reaction was stirred at room temperature for 30 minutes. The reaction was cooled to 0° C., iodomethane (0.07 mL, 1.2 mmol) was added, and the reaction was stirred at room temperature overnight. The reaction was diluted with water and extracted with $CH_2Cl_2$. The organics were dried ($Na_2SO_4$), filtered, and solvent was removed in vacuo. The crude mixture, DMAP (0.004 g, 0.00003 mol) and methanol (0.05 mL, 0.001 mol) were dissolved in 20 mL $CH_2Cl_2$. 1-(3-Dimethylaminopropyl)-3-ethylcarbodiimide hydrochloride (EDC, 0.059 g, 0.0003 mol) was added and the reaction stirred overnight at room temperature. Solvent was removed and the product was purified by silica gel chromatography. Compound 119 was obtained as a colorless oil (0.1 g, 0.00023 mol). $^1$H (CDCl$_3$): 7.3–6.9 (m, 8H), 4.3–4.1 (m, 2H), 3.92 (m, 2H), 3.66 and 3.62 (two singlets, 5H), 2.49 (m, 1H), 2.25 (m, 1H), 1.66 (m, 2H), 1.51 (s, 3H), 1.33 (m, 6H), 0.89 (br t, 3H).

EXAMPLE 37

Compound 128 of Table 2: Benzeneacetic acid, 2-[2-(4-hexyl-3,4-dihydro-2-methyl-3-oxo-2H-1,4-benzoxazin-2-yl)ethoxy]-

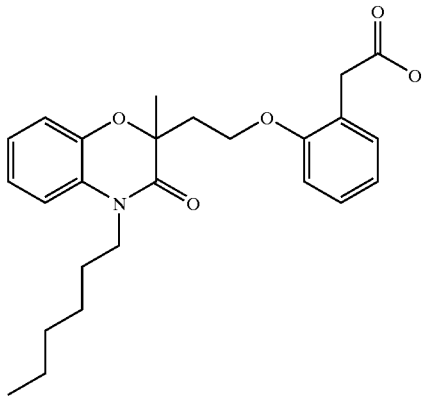

Prepared from Compound 127 (0.1 g, 0.00023 mol) in a manner analogous to Method D. Obtain Compound 120 as a colorless oil (0.078 g, 0.0002 mol). $^1$H (CDCl$_3$): 7.3–6.8 (m, 8H), 4.22 (t, 2H, J=6.8), 3.92 (m, 2H), 3.68 (d, 1H, J=15.5), 3.59 (d, 1H, J=15.1), 2.62 (m, 1H), 2.26 (m, 1H), 1.64 (m, 2H), 1.48 (s, 3H), 1.31 (m, 6H), 0.88 (br t, 3H).

EXAMPLE 38

Compound 132 of Table 3: 2H-1,4-benzoxazin-3(4H)-one, 4-(4-methoxybutyl)-2-[2-[2-(1H-tetrazol-5-ylmethyl)phenoxy]ethyl]-, (2R)-

Compound 132

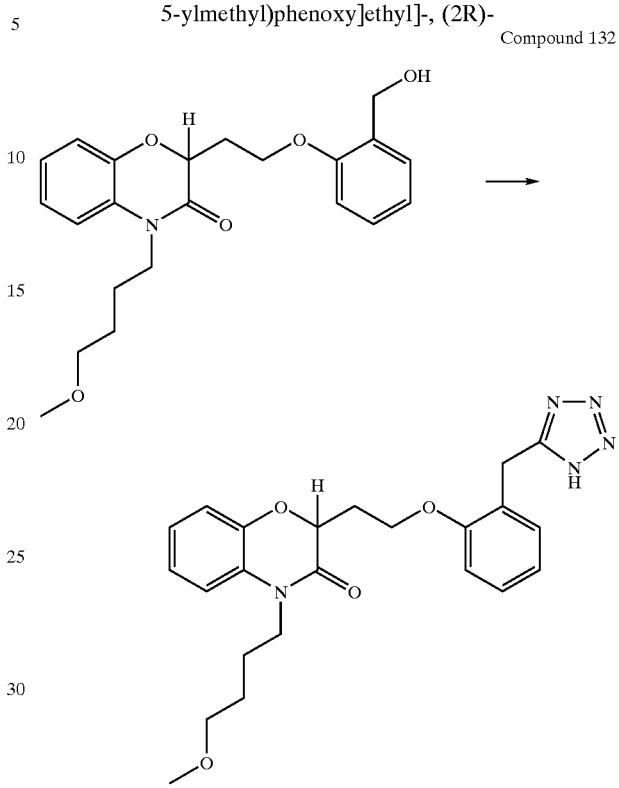

To a solution of the nitrile (370 mg, 0.94 mmol) in toluene (3 mL) was added sodium azide (80 mg, 1.22 mmol) and triethylamine hydrochloride (168 mg, 1.22 mmol). The reaction was heated at 100° C. for 20 h. The mixture was diluted with water and ethyl acetate (10 mL each) and acidified to pH=1 with conc. hydrochloric acid. The organic layer was washed with brine, dried ($Na_2SO_4$) and concentrated in vacuo to give 112 mg of the tetrazole as a white solid. MS: 460 (M+Na).

EXAMPLE 39

Compound 126: Benzeneacetic acid, 2-[2-[3,4-dihydro-3-oxo-4-(6-methanesulfonamidohexyl)-2H-1,4-benzoxazin-2-yl]ethoxy]-

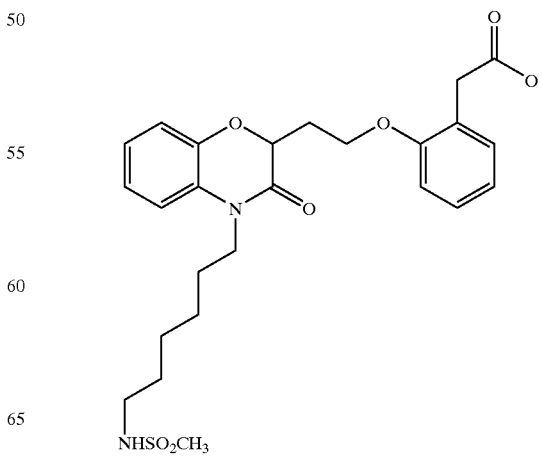

Intermediate 17: 2H-1,4-Benzoxazin-3(4H)-one, 2-[2-[[(1,1-dimethylethyl)dimethylsilyl]oxy]ethyl]-4-(6-hexylphthalimide)-

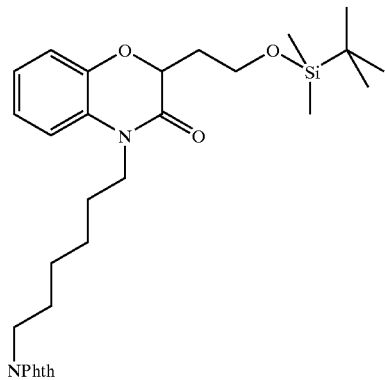

A solution of Intermediate 2 (3.0 g, 9.8 mmol) in 20 mL anh. DMF, under $N_2$, was cooled to 0° C. Sodium hydride (80% dispersion in oil, 0.35 g, 11.7 mmol) was added in two portions of 0.17 g with five minute intervals between additions. The solution was stirred for an additional 40 min at 0° C. 6-bromo-hexylphthalimide (4.0 g, 12.7 mmol) in 5 mL DMF was added dropwise, the ice bath was replaced with an oil bath, and the solution was stirred at 50° C. for 17 h. The mixture was cooled to room temperature and poured into 1.5 L water containing approx. 200 g salt. The aqueous mixture was washed with 4×125 mL of 1:1 diethyl ether/ethyl acetate. The combined organics were washed with 6×125 mL water and 125 mL brine. The organics were dried ($Na_2SO_4$), filtered, and solvent was removed in vacuo. The product was isolated by silica gel chromatography with hexane/ethyl acetate. Intermediate 17 was obtained as a colorless oil (5.2 g, 9.8 mmol). MS: 559 (M+Na)

Intermediate 18: (2H-1,4-Benzoxazin-3(4H)-one, 2-(2-hydroxyethyl)-4-(6-hexylphthalimide)-

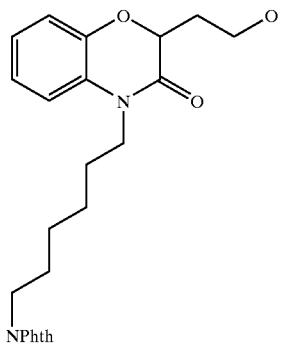

Intermediate 17 (6.2 g) was dissolved in 150 mL methanol and 20 mL water. Methanesulfonic acid (4 mL) was added and the mixture was stirred at room temperature for 2 h. Solvent was removed in vacuo and the product was isolated by silica gel chromatography with hexane/ethyl acetate. Intermediate 18 was obtained as a colorless oil (5.0 g, 11.4 mmol). MS: 445 (M+Na).

Intermediate 19: Benzeneacetic acid, 2-[2-[3,4-dihydro-3-oxo-4-(6-hexylphthalimide)-2H-1,4-benzoxazin-2-yl]ethoxy]-, methyl ester

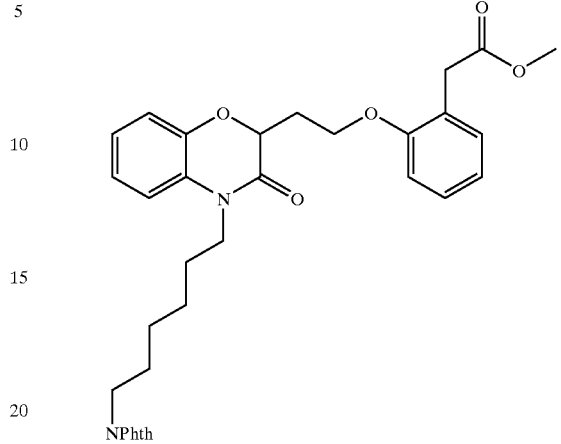

A solution of Intermediate 18 (5 g, 11.8 mmol), methyl (2-hydroxyphenyl)acetate (3.9 g, 17.8 mmol), and tributylphosphine (4.4 mL, 17.8 mmol) in 180 mL anhydrous benzene, under $N_2$, was cooled to 4° C. 1,1'-(Azodicarbonyl)dipiperidine (4.5 g, 17.8 mmol) in THF (36 mL) was added in one portion, and the solution was stirred, at room temperature overnight. The organic phase was washed with 4×20 mL 2 N NaOH, 40 mL water and 40 mL brine. The organics were dried ($Na_2SO_4$), filtered, and solvent was removed in vacuo. The product was purified by silica gel chromatography with hexane/ethyl acetate. Compound 77 was obtained as a yellow solid (2.6 g, 4.56 mmol). MS: 593 (M+Na)

Intermediate 20: Benzeneacetic acid, 2-[2-[3,4-dihydro-3-oxo-4-(6-methylsulfonamidohexyl)-2H-1,4-benzoxazin-2-yl]ethoxy]-, methyl ester

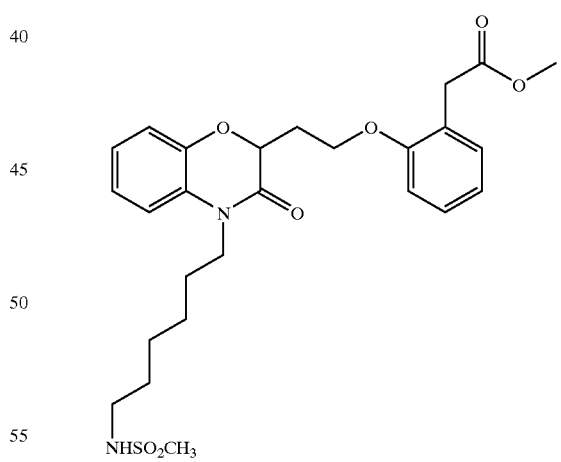

To a suspension of intermediate 19 (1.0 g, 1.75 mmol) in 3.5 mL EtOH and 2 mL THF was added hydrazine (0.07 mL, 2.1 mmol). The reaction was stirred overnight at room temperature, then diluted with MeOH and filtered. The solvent is evaporated in vacuo to give a white solid. To the white solid (0.2 g, 0.45 mmol) in 4 mL of $CH_2Cl_2$ is added methanesulfonyl chloride (0.04 mL, 0.6 mmol) and triethylamine (0.1 mL, 0.74 mmol). The reaction is stirred for 17h at room temperature, then quenched with 2 mL of 1N HCl and diluted with 8 mL of EtOAc. The organic layer is washed with water and brine, dried (Na₂SO₄) and concentrated in vacuo. Purification by reverse-phase HPLC gave intermediate 20 as an orange oil (0.038 g, 0.07 mmol). MS: 541 (M+Na).

Compound 126: Benzeneacetic acid, 2-[2-[3,4-dihydro-3-oxo-4-(6-methanesulfonamidohexyl)-2H-1,4-benzoxazin-2-yl]ethoxy]-

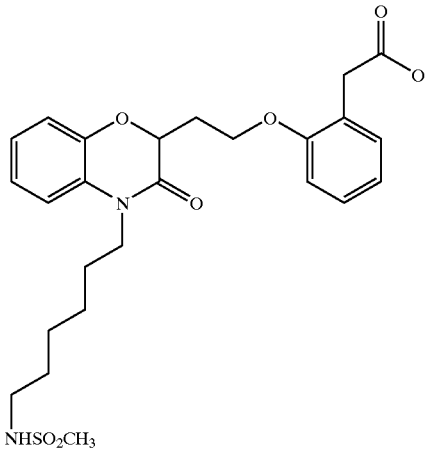

A solution of Intermediate 20 (0.038 g, 0.07 mmol) in 5 mL MeOH was cooled to 0° C. NaOH (0.04 g, 1 mmol) in 1 mL water was added and the 3solution was stirred at room temperature overnight. The solution was acidified to pH=5 with 1N HCl. The mixture is extracted with ethyl acetate. The combined organics were washed with water/brine combination, dried (Na₂SO₄), and filtered. Compound 126 was obtained as a yellow oil (0.03 g, 0.06, mmol). MS: 527 (M+Na).

Additional compounds in Tables 1, 2, and 3 below were made in the manners similar to the above examples and schemes.

aP2 Assay for Antagonist

Twenty-four hours after the initial seeding of the 96-well plates by hand (around 20,000/well), the differentiation assay may be initiated. Medium may be removed and replaced with 150μl of differentiation medium containing vehicle (DMSO) or test compounds with a known aP2 activator or such aP2 activator alone. Cells may be returned to incubator for 24 hours culture. At the termination of the challenge, medium may be removed and 100 μl of lysis buffer may be added to initiate the bDNA aP2 mRNA assay. The branched DNA assay may be performed according to the manufacturer's protocol (Bayer Diagnostics; Emeryville, Calif.). Result may be expressed as percent inhibition of aP2 mRNA production activated by the aP2 activator. $IC_{50}$'s may be determined by non-linear regression with a sigmoidal fit curve.

Following the challenge of the preadipocytes, cells may be lysed with lysis buffer (Bayer Diagnostics) containing the aP2 oligonucleotides. After a 15 minutes incubation at 53° C. or 30 minutes at 37° C. incubator, 70 μl of the lysis buffer from each well may, be added to a corresponding capture well (preincubated with 70 μl of blocking buffer (Bayer Diagnostics)). The capture plate may be incubated overnight at 53° C. in a plate incubator (Bayer Diagnostics). After this incubation, the bDNA and labeled probes may be annealed as directed by the manufacturer. Following a 30-minute incubation with the luminescent alkaline phosphatase substrate, dioxitane, the luminescence may be quantitated in a Dynex MLX microtiter plate luminometer. Oligonucleotide probes designed to anneal to the aP2 mRNA and function in the bDNA mRNA detection system are designed with ProbeDesigner software (Bayer Diagnostics). This software package analyzes a target sequence of interest with a series of algorithms in order to determine which regions of the sequence can perform as locations for capture, label, or spacer probe annealing. The sequences of the oligonucleotides are as follows:

SEQ ID NO.1 CATTTTGTGAGTTTTCTAGGATTAT-TCTTTTCTCTTGGAAAGAAAGT

SEQ ID NO.2 ATGTTAGGTTTGGCCATGC-CTTTCTCTTGGAAAGAAAGT

SEQ ID NO.3 CCTCTCGTTTTCTCTTTATG-GTTTTCTCTTGGAAAGAAAGT

SEQ ID NO.4 GCTTATGCTCTCTCAT-AAACTCTCGTGGTTTCTCTTGGAAAGAAAGT

SEQ ID NO.5 CCAGGTACCTACAAAAGCATCA-CATTTAGGCATAGGACCCGTGTCT

SEQ ID NO.6 GCCCACTCCTACTTCTTTCATATAAT-CATTTAGGCATAGGACCCGTGTCT

SEQ ID NO.7 AGCCACTTTCCTGGTGGCAAATT-TAGGCATAGGACCCGTGTCT

SEQ ID NO.8 CATCCCCATTCACACTGATGATCTT-TAGGCATAGGACCCGTGTCT

SEQ ID NO.9 GTACCAGGACACCCCCATCTAAG-GTTTTTAGGCATAGGACCCGTGTCT

SEQ ID NO.10 GGTTGATTTTCCATCCCATTTCTG-CACATTTTAGGCATAGGACCCGTGTCT

SEQ ID NO.11 GCATTCCACCACCAGTTTATCATTT-TAGGCATAGGACCCGTGTCT

SEQ ID NO.12 GCGAACTTCAGTCCAGGT-CAACGTCCCTTGTTTAGGCATAGGAC-CCGTGTCT

SEQ ID NO.13 TCCCACAGAATGTTGTAGAGT-TCTTTTAGGCATAGGACCCGTGTCT

SEQ ID NO.14 AAAACAACAATATCTTTTTGAA-CAATATATTTAGGCATAGGACCCGTGTCT

SEQ ID NO.15 TCAAAGTTTTCACTGGAGA-CAAGTTT

SEQ ID NO.16 AAAGGTACTTTCAGATTTAATGGT-GATCA

SEQ ID NO.17 CTGGCCCAGTATGAAGGAAATCT-CAGTATTTTT

SEQ ID NO.18 TCTGCAGTGACTTCGTCAAATTC

SEQ ID NO.19 ATGGTGCTCTTGACTTTCCTGTCA

SEQ ID NO.20 AAGTGACGCCTTTCATGAC aP2 Assay for Agonist

The procedure is described in detail in Burris et al., Molecular Endocrinology, 1999, 13:410, which is hereby incorporated by reference in its entirety, and aP2 assay results of agonist intrinsic activity may be presented as fold increase over vehicle in induction of aP2 mRNA production. Tables 1, 2, and 3 below set forth the mass spectra data and the agonist intrinsic activity of some compounds of the present invention.

TABLE 1

Compounds of this invention wherein $Z^1$ and $Z^2$ are both H

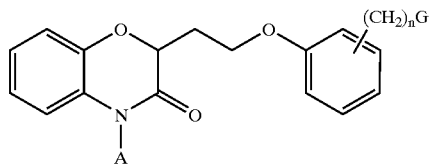

| Compound No. | A | Pos(n)G | MS; $MH^+$/Na | Agonist Intrinsic Activity |
|---|---|---|---|---|
| 1 | 4-MeBn | 2(0)COOCH$_3$ | 432 | 0.9 |
| 2 | 3-MeBn | 2(0)CF$_3$ | 442 | 1.2 |
| 3 | 3-MeBn | 2(0)COOCH$_3$ | 432 | 0.6 |
| 4 | Bn | 2(0)COOCH$_3$ | 418 | 1.0 |
| 5 | 4-ClBn | 2(0)COOCH$_3$ | 452 | 0.7 |
| 6 | 3-ClBn | 2(0)COOCH$_3$ | 452 | — |
| 7 | 3,5-Cl$_2$Bn | 2(0)COOCH$_3$ | 486 | — |
| 8 | 3,4-Cl$_2$Bn | 2(0)CF$_3$ | 497 | 3.3 |
| 9 | 3-CF$_3$Bn | 2(0)COOCH$_3$ | 486 | 0.9 |
| 10 | 3-CF$_3$Bn | 2(0)CF$_3$ | 496 | 0.8 |
| 11 | n-Hex | 2(1)CONH$_2$ | 411 | — |
| 12 | n-Hex | 2(0)C(O)COOCH$_3$ | 440 | — |
| 13 | n-Hex | 2(0)C(O)COOH | 426 | 2.6 |
| 14 | n-Hex | 2(1)P(O)(OEt)$_2$ | 503 | 1.6 |
| 15 | n-Hex | 2(1)P(O)(OH)$_2$ | 448 | 7.2 |
| 16 | n-Hex | 2(0)CF$_3$ | 422 | — |
| 17 | n-Dec | 2(0)CF$_3$ | 478 | 1.1 |
| 18 | MeO(CH$_2$)$_4$ | 2(0)CF$_3$ | 424 | 0.3 |
| 19 | EtO(CH$_2$)$_3$ | 2(0)CF$_3$ | 424 | 1.4 |
| 20 | Me(CH$_2$)$_2$O(CH$_2$)$_2$ | 2(0)CF$_3$ | 424 | 1.2 |
| 21 | Me(CH$_2$)$_2$S(CH$_2$)$_2$ | 2(0)CF$_3$ | 440 | 1.9 |
| 22 | MeOC(O)CH$_2$ | 2(1)COOCH$_3$ | 414 | 7.2 |
| 23 | HOC(O)CH$_2$ | 2(1)COOH | 386 | 0.8 |
| 24 | AcOCH$_2$CH$_2$ | 2(1)COOCH$_3$ | 428 | 1.3 |
| 25 | HOCH$_2$CH$_2$ | 2(1)COOH | 371 | 3.5 |
| 26 | 3-CF$_3$Bn | 2(0)COONa | 472 | 3.1 |
| 27 | 3-CF$_3$Bn | 2(1)COOCH$_3$ | 500 | 0.8 |
| 28 | 3-CF$_3$Bn | 2(1)COONa | 486 | 21.5 |
| 29 | 3-CF$_3$Bn | 2(2)COOCH$_3$ | 514 | 0.8 |
| 30 | 3-CF$_3$Bn | 2(2)COONa | 500 | 5.6 |
| 31 | 3-CF$_3$Bn | 2(3)COOCH$_3$ | 528 | 0.9 |
| 32 | 3-CF$_3$Bn | 2(3)COONa | 514 | 8.2 |
| 33 | 3-CF$_3$Bn | 3(1)COOCH$_3$ | 500 | 0.8 |
| 34 | 3-CF$_3$Bn | 3(1)COONa | 486 | 10.4 |
| 35 | 3-CF$_3$Bn | 3(2)COOCH$_3$ | 514 | 0.8 |
| 36 | 3-CF$_3$Bn | 3(2)COONa | 500 | 11.1 |
| 37 | 4-CF$_3$Bn | 2(1)COOCH$_3$ | 500 | 1.2 |
| 38 | 4-CF$_3$Bn | 2(1)COOH | 486 | 38.7 |
| 39 | 3,5-(CF$_3$)$_2$Bn | 2(1)COOCH$_3$ | 568 | — |
| 40 | 3,5-(CF$_3$)$_2$Bn | 2(1)COOH | 554 | 6.7 |
| 41 | 3,5-(CF$_3$)$_2$Bn | 2(2)COOCH$_3$ | 582 | — |
| 42 | 3,5-(CF$_3$)$_2$Bn | 2(2)COOH | 568 | 2.1 |
| 43 | 3,5-(CF$_3$)$_2$Bn | 3(1)COOCH$_3$ | 568 | — |
| 44 | 3,5-(CF$_3$)$_2$Bn | 3(1)COOH | 554 | 6.8 |
| 45 | MeOC(O)CH$_2$ | 2(1)COOCH$_3$ | 414 | 7.2 |
| 46 | HOC(O)CH$_2$ | 2(1)COOH | 386 | 2 |
| 47 | AcOCH$_2$CH$_2$ | 2(1)COOCH$_3$ | 428 | 1.3 |
| 48 | HOCH$_2$CH$_2$ | 2(1)COOH | 371 | 8 |
| 49 | propargyl | 2(1)COOCH$_3$ | 380 | 5.7 |
| 50 | n-Hept | 2(1)COOCH$_3$ | 440 | 6.2 |
| 51 | n-Hept | 2(1)COOH | 426 | 28.6 |
| 52 | n-Oct | 2(1)COOCH$_3$ | 454 | 1.3 |
| 53 | n-Oct | 2(1)COOH | 440 | 26.4 |
| 54 | n-Non | 2(1)COOCH$_3$ | 468 | 0.9 |
| 55 | n-Non | 2(1)COOH | 454 | 7.1 |
| 56 | n-Dec | 2(1)COOCH$_3$ | 482 | 1.0 |
| 57 | n-Dec | 2(1)COOH | 468 | 9.9 |
| 58 | PhCH$_2$OC(O)(CH$_2$)$_4$ | 2(1)COOCH$_3$ | 532 | — |
| 59 | HOC(O)(CH$_2$)$_4$ | 2(1)COOCH$_3$ | 442 | — |
| 60 | HOC(O)(CH$_2$)$_4$ | 2(1)COOH | 428 | 1.5 |
| 61 | H$_2$NC(O)(CH$_2$)$_4$ | 2(1)COOCH$_3$ | 441 | — |
| 62 | H$_2$NC(O)(CH$_2$)$_4$ | 2(1)COOH | 427 | 1.5 |
| 63 | HO(CH$_2$)$_5$ | 2(1)COOCH$_3$ | 428 | — |

TABLE 1-continued

Compounds of this invention wherein $Z^1$ and $Z^2$ are both H

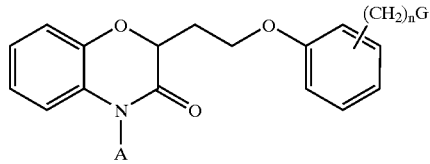

| Compound No. | A | Pos(n)G | MS; MH+/Na | Agonist Intrinsic Activity |
|---|---|---|---|---|
| 64 | HO(CH$_2$)$_5$ | 2(1)COOH | 414 | 3.6 |
| 65 | c-HexCH$_2$CH$_2$ | 2(1)COOCH$_3$ | 452 | 0.8 |
| 66 | c-HexCH$_2$CH$_2$ | 2(1)COOH | 438 | 6.8 |
| 67 | c-PentCH$_2$CH$_2$ | 2(1)COOCH$_3$ | 438 | — |
| 68 | c-PentCH$_2$CH$_2$ | 2(1)COOH | 424 | 43.2 |
| 69 | c-Pent(CH$_2$)$_3$ | 2(1)COOCH$_3$ | 452 | — |
| 70 | c-Pent(CH$_2$)$_3$ | 2(1)COOH | 438 | 57.9 |
| 71 | Me$_2$CH(CH$_2$)$_4$ | 2(1)COOCH$_3$ | 440 | — |
| 72 | Me$_2$CH(CH$_2$)$_4$ | 2(1)COOH | 426 | 32 |
| 73 | Me$_3$C(CH$_2$)$_4$ | 2(1)COOCH$_3$ | 454 | — |
| 74 | Me$_3$C(CH$_2$)$_4$ | 2(1)COOH | 440 | 22.0 |
| 75 | Me$_3$CCH$_2$CH(Me)(CH$_2$)$_2$ | 2(1)COOCH$_3$ | 468 | — |
| 76 | Me$_3$CCH$_2$CH(Me)(CH$_2$)$_2$ | 2(1)COOH | 454 | 28.7 |
| 77 | MeC(O)(CH$_2$)$_4$ | 2(1)COOCH$_3$ | 440 | 9.9 |
| 78 | MeC(O)(CH$_2$)$_4$ | 2(1)COOH | 426 | 11.1 |
| 79 | MeC(NOH)(CH$_2$)$_4$ | 2(1)COOH | 441 | 4.5 |
| 80 | MeC(NOMe)(CH$_2$)$_4$ | 2(1)COOH | 455 | 2.8 |
| 81 | MeCH(OH)(CH$_2$)$_4$ | 2(1)COOCH$_3$ | 442 | — |
| 82 | MeCH(OH)(CH$_2$)$_4$ | 2(1)COOH | 428 | 4.9 |
| 83 | Me$_2$C(OH)(CH$_2$)$_4$ | 2(1)COOCH$_3$ | 456 | — |
| 84 | Me$_2$C(OH)(CH$_2$)$_4$ | 2(1)COOH | 442 | 3.5 |
| 85 | MeCH(NH(Ac))(CH$_2$)$_4$ | 2(1)COOH | 469 | 24 |
| 86 | MeCF$_2$(CH$_2$)$_4$ | 2(1)COOCH$_3$ | 462 | — |
| 87 | MeCF$_2$(CH$_2$)$_4$ | 2(1)COOH | 448 | 37.9 |
| 88 | enant 1; MeCF$_2$(CH$_2$)$_4$ | 2(1)COOH | 448 | 45.4 |
| 89 | enant 2; MeCF$_2$(CH$_2$)$_4$ | 2(1)COOH | 448 | 42.0 |
| 90 | F(CH$_2$)$_6$ | 2(1)COOCH$_3$ | 444 | — |
| 91 | F(CH$_2$)$_6$ | 2(1)COOH | 430 | 64.9 |
| 92 | enant 1; F(CH$_2$)$_6$ | 2(1)COOH | 430 | 44.8 |
| 93 | enant 2; F(CH$_2$)$_6$ | 2(1)COOH | 430 | 53.1 |
| 94 | HO(CH$_2$)$_6$ | 2(1)COOCH$_3$ | 442 | — |
| 95 | HO(CH$_2$)$_6$ | 2(1)COOH | 428 | 36.9 |
| 96 | H$_2$NCH$_2$CMe$_2$(CH$_2$)$_4$ | 2(1)COOH | 455 | 27.5 |
| 97 | H$_2$NC(O)(CH$_2$)$_5$ | 2(1)COOCH$_3$ | 455 | — |
| 98 | H$_2$NC(O)(CH$_2$)$_5$ | 2(1)COOH | 441 | 28 |
| 99 | PhCH$_2$OC(O)(CH$_2$)$_5$ | 2(1)COOCH$_3$ | 546 | — |
| 100 | HOC(O)(CH$_2$)$_5$ | 2(1)COOCH$_3$ | 456 | — |
| 101 | HOC(O)(CH$_2$)$_5$ | 2(1)COOH | 442 | 3.0 |
| 102 | HOC(O)CMe$_2$(CH$_2$)$_4$ | 2(1)COOH | 470 | 4.1 |
| 103 | NCCMe$_2$(CH$_2$)$_4$ | 2(1)COOCH$_3$ | 465 | — |
| 104 | NCCMe$_2$(CH$_2$)$_4$ | 2(1)COOH | 451 | 26.5 |
| 105 | MeCF$_2$(CH$_2$)$_5$ | 2(1)COOCH$_3$ | 476 | — |
| 106 | MeCF$_2$(CH$_2$)$_5$ | 2(1)COOH | 462 | 40.8 |
| 107 | MeC(O)(CH$_2$)$_5$ | 2(1)COOCH$_3$ | 454 | — |
| 108 | MeC(O)(CH$_2$)$_5$ | 2(1)COOH | 440 | 37.3 |
| 109 | F(CH$_2$)$_7$ | 2(1)COOCH$_3$ | 458 | — |
| 110 | F(CH$_2$)$_7$ | 2(1)COOH | 444 | 64.5 |
| 111 | AcO(CH$_2$)$_7$ | 2(1)COOCH$_3$ | 498 | — |
| 112 | HO(CH$_2$)$_7$ | 2(1)COOH | 442 | 74.5 |
| 113 | F(CH$_2$)$_5$ | 2(1)COOH | 416 | 29.1 |
| 114 | MeO(CH$_2$)$_4$ | 2(1)COOH | 414 | 50.7 |
| 115 | EtO(CH$_2$)$_3$ | 2(1)COOH | 414 | 40.9 |
| 116 | PrS(CH$_2$)$_2$ | 2(1)COOH | 430 | 4.0 |
| 117 | PrO(CH$_2$)$_2$ | 2(1)COOH | 414 | 45.9 |
| 118 | 3,4-Cl$_2$Ph | 2(1)COOCH$_3$ | 486 | 0.9 |
| 119 | 3,4-Cl$_2$Ph | 2(1)COOH | 472 | 22.8 |

TABLE 1-continued

Compounds of this invention wherein $Z^1$ and $Z^2$ are both H

| Compound No. | A | Pos(n)G | MS; $MH^+$/Na | Agonist Intrinsic Activity |
|---|---|---|---|---|
| 120 | 2-phenyl-5-methyl-oxazol-4-yl-(CH$_2$)- | 2(1)COOH | 513 | 22.5 |
| 121 | n-Hex | 4(0)SC(CH$_3$)$_2$COOH | 472 | 16.13 |
| 122 | CH$_3$(CH$_2$)$_2$NHCOCH$_2$ | 2(1)COOH | 449 (M + Na) | 40.83 |
| 123 | n-Hex | 4(0) 4-acetylpiperazin-1-yl | 480 | 1.65 |
| 124 | CH$_3$NHCO(CH$_2$)$_3$ | 2(1)COOH | 449 (M + Na) | 4.00 |
| 125 | CH$_3$CONH(CH$_2$)$_6$ | 2(1)COOH | 491 (M + Na) | 10.78 |
| 126 | CH$_3$SO$_2$NH(CH$_2$)$_6$ | 2(1)COOH | 527 (M + Na) | 12.96 |

Keys:
Me = methyl; Et = ethyl; Pr = propyl; Bu = butyl; Pent = pentyl; Hex = hexyl; Hept = heptyl; Oct = octyl; Non = nonyl; Dec = decyl; Ac = acetyl; Bn = benzyl.

TABLE 2

Amides of this invention

| Compound No. | Structure | MS; $MH^+$ | Agonist Intrinsic Activity |
|---|---|---|---|
| 127 | 2-methyl-benzoxazinone with N-hexyl and 2-(CH$_2$COOCH$_3$)phenoxyethyl substituent | 440 | — |

TABLE 2-continued
Amides of this invention
| Compound No. | Structure | MS; MH+ | Agonist Intrinsic Activity |
|---|---|---|---|
| 128 | 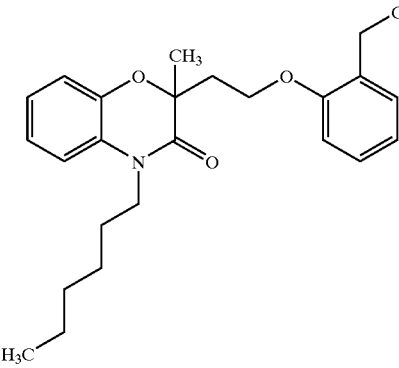 | 426 | 2.5 |
TABLE 3
Some stereoisomers of the invention
| Compound No. | Structure | MS (MH+/ M + Na) | PPAR γ Agonist Intrinsic Activity |
|---|---|---|---|
| 129 | 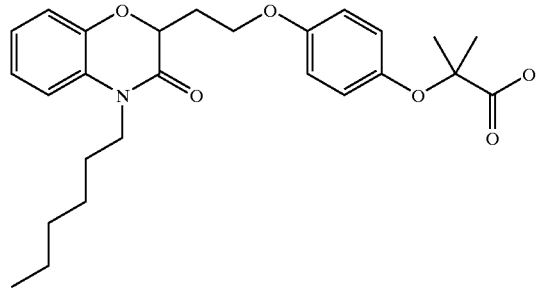 Chiral | 456 (M + H) | 12.62 |
| 130 | 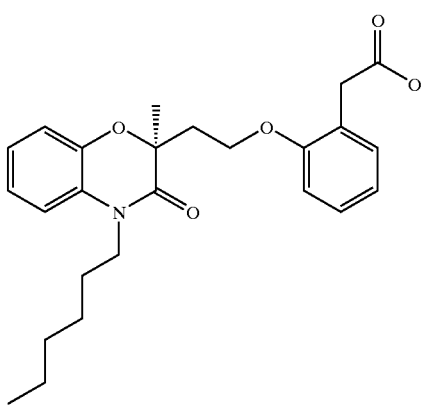 Chiral | 448 (M + Na) | 91.3 |

TABLE 3-continued

Some stereoisomers of the invention

| Compound No. | Structure | MS (MH+/ M + Na) | PPAR γ Agonist Intrinsic Activity |
|---|---|---|---|
| 131 | 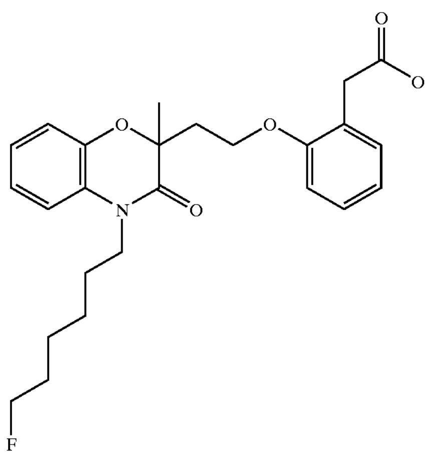 | 466 (M + Na) | 36.4 |
| 132 | 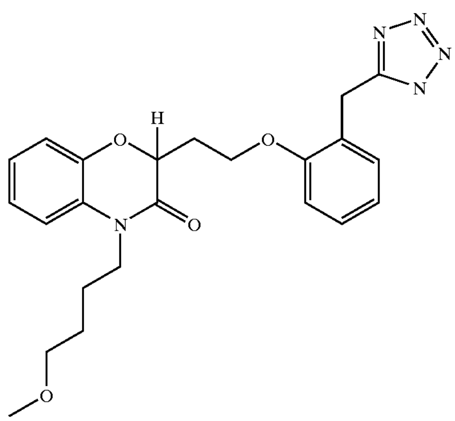 | 460 (M + Na) | |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

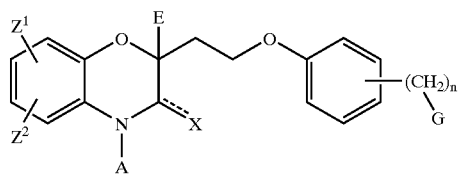

or an optical isomer, enantiomer, diastereomer, racemate or racemic mixture thereof, ester, prodrug form, or a pharmaceutically acceptable salt thereof, wherein A is selected from aryl, heterocyclyl, and $C_1$–$C_{10}$ alkyl, said aryl, heterocyclyl, and $C_1$–$C_{10}$ alkyl being optionally substituted with one or more members selected from the group consisting of halogen, OH, aryl, $C_3$–$C_8$ cycloalkyl, $C_1$–$C_{10}$ alkyl substituted with a halogen, $C_1$–$C_{10}$ alkyl ether, heterocyclyl, carbonyl, oxime, —N($R^1$)($SO_2$R), —C($NNR^3R^4$)$R^1$, —COO$R^1$, —CON$R^1R^2$, —OC(O)$R^1$, —OC(O)O$R^1$, —OC(O)N$R^1R^2$, —N$R^1R^2$, —N$R^3$C(O)$R^1$, —N$R^3$C(O)O$R^1$, and —N$R^3$C(O)N$R^1R^2$, wherein R is selected from $C_1$–$C_6$ alkyl, trifluoromethyl, phenyl, and substituted phenyl;

$R^1$ and $R^2$ are independently selected from hydrogen, $C_1$–$C_{10}$ alkyl, aryl, heterocyclyl, and alkylaryl, or $R^1$ and $R^2$ may be taken together to form a 5- to 10-member ring; and $R^3$ and $R^4$ are independently selected from hydrogen, $C_1$–$C_{10}$ alkyl, aryl, heterocyclyl, alkylaryl, —C(O)$R^1$, or —C(O)N$R^1R^2$;

$Z^1$ is selected from hydrogen, $C_1$–$C_6$ alkyl, aryl, heterocyciyl, COO$R^1$, CON$R^1R^2$, OH, $C_1$–$C_6$ alkyl ether, —OC(O)$R^1$, —OC(O)O$R^1$, —OC(O)N$R^1R^2$, —N$R^1R^2$, —N$R^3$C(O)$R^1$, —N$R^3$C(O)O$R^1$, —N$R^3$C(O)N$R^1R^2$, halogen, —C(O)$R^1$, —C(N$R^3$)$R^1$, —C(NO$R^3$)$R^1$, and —C(NN$R^3R^4$)$R^1$;

$Z^2$ is selected from hydrogen, halogen, $C_1$–$C_6$ alkyl;

$Z^1$ and $Z^2$ may together form a fused aromatic ring;

n is an integer from 0 to 3;

G is selected from —COO$R^1$, —C(O)COO$R^1$, —CON$R^1R^2$, —CF$_3$, —P(O)(O$R^1$)(O$R^2$), —S—$R^8$, —O—$R^8$,

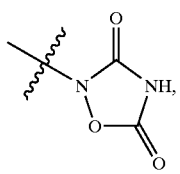 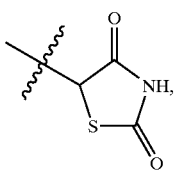 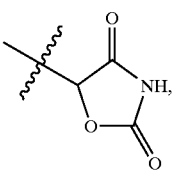

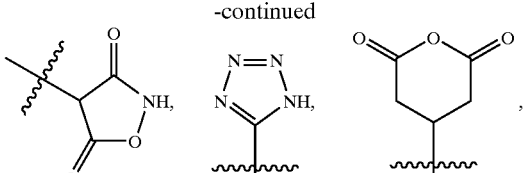

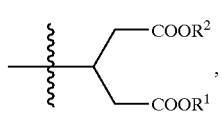

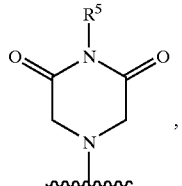

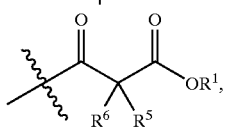

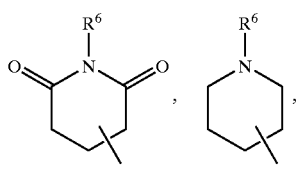 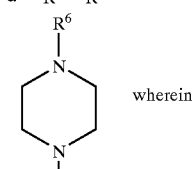

$R^5$ and $R^6$ are independently hydrogen or $C_1$–$C_6$ alkyl;

$R^7$ is hydrogen, $C_1$–$C_6$ alkyl, or —C(O)$R^5$;

$R^8$ is selected from the group consisting of hydrogen, $C_1$–$C_6$ alkyl, and substituted $C_1$–$C_6$ alkyl; and B is oxygen or —N$R^5$;

E is selected from hydrogen, $C_1$–$C_6$ alkyl and a moiety of the formula

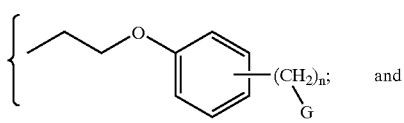

X is hydrogen or oxygen, with the proviso that when E is hydrogen and G is —COOH, —COOCH$_3$, or a moiety of the formula of A is selected from the group consisting of aryl, heterocyclyl, substituted $C_1$–$C_6$ alkyl and $C_7$–$C_{10}$ alkyl, provided that when X is hydrogen, n is 1 and G is a moiety of the formula of A is selected from the group consisting of heterocyclyl, and $C_7$–$C_{10}$ alkyl.

2. A compound of claim 1 wherein

A is selected from aryl, heterocyclyl, and $C_1$–$C_{10}$ alkyl, said aryl, heterocyclyl, and $C_1$–$C_{10}$ alkyl being optionally substituted with one or more members selected from the group consisting of halogen, OH, aryl, $C_3$–$C_8$ cycloalkyl, $C_1$–$C_{10}$ alkyl substituted with a halogen, $C_1$–$C_{10}$ alkyl ether, heterocyclyl, carbonyl, oxime, —C(NNR$^3$R$^4$)R$^1$, —COOR$^1$, —CONR$^1$R$^2$, —OC(O)R$^1$, —OC(O)OR$^1$, —OC(O)NR$^1$R$^2$, —NR$^1$R$^2$, —NR$^3$C(O)R$^1$, —NR$^3$C(O)OR$^1$, and —NR$^3$C(O)NR$^1$R$^2$, wherein R$^1$ and R$^2$ are independently selected from hydrogen, $C_1$–$C_{10}$ alkyl, aryl, heterocyclyl, and alkylaryl, or R$^1$ and R$^2$ may be taken together to form a 5- to 10-member ring; and R$^3$ and R$^4$ are independently selected from hydrogen, $C_1$–$C_{10}$ alkyl, aryl, heterocyclyl, alkylaryl, —C(O)R$^1$, or —C(O)NR$^1$R$^2$;

and

G is selected from —COOR$^1$, —C(O)COOR$^1$, —CONR$^1$R$^2$, —CF$_3$, —P(O)(OR$^1$)(OR$^2$), —S—R$^8$, R$^5$ and R$^6$ are independently hydrogen or $C_1$–$C_6$ alkyl;

R$^7$ is hydrogen, $C_1$–$C_6$ alkyl, or —C(O)R$^5$;

R$^8$ is selected from the group consisting of hydrogen, $C_1$–$C_6$ alkyl, and substituted $C_1$–$C_6$ alkyl; and B is oxygen or —NR$^5$.

3. A compound of claim 1 wherein X is oxygen.

4. A compound of claim 1 wherein E is $C_1$–$C_6$ alkyl or a moiety of the formula wherein G and n are as claimed in claim 1.

5. A compound of claim 1 wherein A is optionally substituted $C_1$–$C_6$ alkyl or optionally substituted aryl.

6. A compound of claim 5 wherein A is substituted $C_1$–$C_6$ alkyl and G is —COOH or —COOCH$_3$.

7. A compound of claim 1 wherein

A is optionally substituted $C_1$–$C_6$ alkyl or optionally substituted aryl;

X is oxygen; and

G is selected from —COOR$^1$, —CONR$^1$R$^2$, —CF$_3$,

—P(O)(OR¹)(OR²), —S—R⁸, —O—R⁸, and

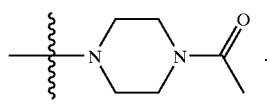

8. A compound of claim 7 wherein

A is $C_1$–$C_6$ alkyl or aryl, said $C_1$–$C_6$ alkyl or aryl being optionally substituted with one or more members selected from the group consisting of halogen, OH, aryl, $C_3$–$C_8$ cycloalkyl, $C_1$–$C_{10}$ alkyl substituted with a halogen, $C_1$–$C_{10}$ alkyl ether, heterocyclyl, carbonyl, oxime, —C(NNR³R⁴)R¹, —COOR¹, —CONR¹R², —OC(O)R¹, —OC(O)OR¹, —OC(O)NR¹R², —NR¹R², —NR³C(O)R¹, —NR³C(O)OR¹, and —NR³C(O)NR¹R²; and G is selected from —COOR¹, —CONR¹R², —CF₃,

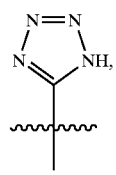

—P(O)(OR¹)(OR²), —S—R⁸, and

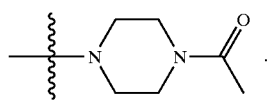

9. A compound of claim 1 which is selected from

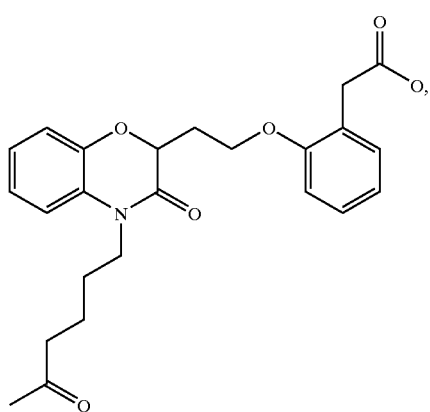

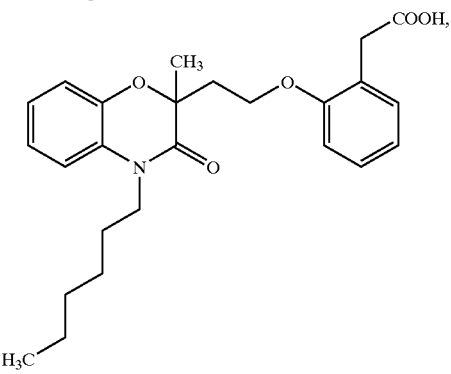

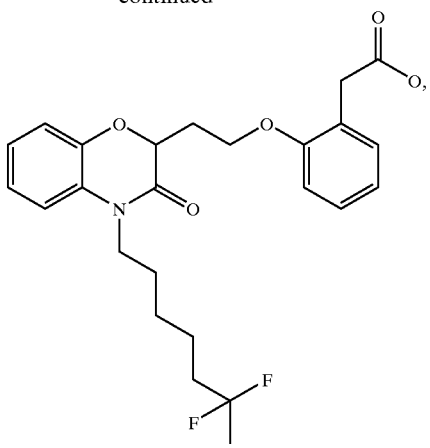

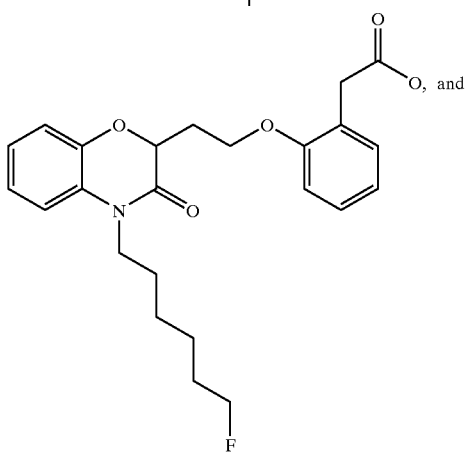

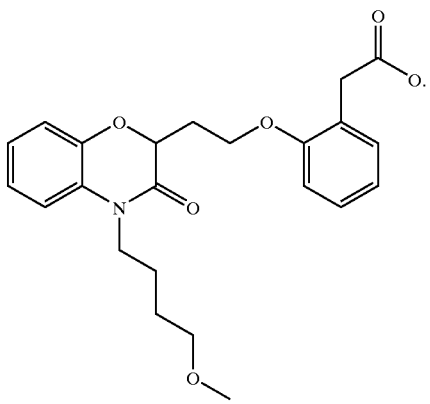

10. A pharmaceutical composition comprising a compound of claim 1 and a pharmaceutically acceptable carrier.

11. A method of treating a subject suffering from a disorder in glucose and lipid metabolism, which comprises administering to the subject a therapeutically effective amount of a compound of claim 1.

12. A method of inhibiting in a subject the onset of a disorder in glucose and lipid metabolism, which comprises administering to the subject a prophylactically effective dose of a compound according to claim 1.

13. A method of claim 11 or 12 wherein said disorder is a condition of reduced insulin sensitivity.

14. A method of claim 13 wherein said condition of reduced insulin sensitivity is Non-Insulin Dependent Diabetes Mellitus.

15. A method of claim 11 or 12 wherein said disorder is selected from Non-Insulin Dependent Diabetes Mellitus, obesity, nephropathy, neuropathy, retinopathy, atherosclerosis, polycystic ovary syndrome, ischemia, hypertension, stroke, and heart disease.

16. A method of claim 15 wherein said condition is Non-insulin Dependent Diabetes Mellitus.

17. A method of claim 15 wherein said condition is obesity.

18. A method of claim 15 wherein said condition is hypertension.

19. A process for making a pharmaceutical composition comprising mixing any of the compounds according to claim 1 and a pharmaceutically acceptable carrier.

* * * * *

SEQUENCE LISTING

<160> NUMBER OF SEQ ID NOS: 15

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 1
cattttgtga gttttctagg attattcttt tctcttggaa agaaagt         47

<210> SEQ ID NO 2
<211> LENGTH: 39

```
<212> TYPE: DNA
<213> ORGANISM: Artificial Sequence
<220> FEATURE:
<223> OTHER INFORMATION: Description of Artificial Sequence: primer

<400> SEQUENCE: 2
atgttaggtt tggccatgcc tttctcttgg aaagaaagt                              39

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 3
cctctcgttt tctctttatg gttttctctt ggaaagaaag t                           41

<210> SEQ ID NO 4
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 4
gcttatgctc tctcataaac tctcgtggtt tctcttggaa agaaagt                     47

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 5
ccaggtacct acaaaagcat cacatttagg cataggaccc gtgtct                      46

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 6
gcccactcct acttctttca tataatcatt taggcatagg acccgtgtct                  50

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 7
agccactttc ctggtggcaa atttaggcat aggacccgtg tct                         43

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 8
```
catccccatt cacactgatg atctttaggc ataggacccg tgtct                45

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 9
gtaccaggac accccatct aaggtttta ggcataggac ccgtgtct                48

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 10
ggttgatttt ccatcccatt tctgcacatt ttaggcatag gacccgtgtc t           51

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 11
gcattccacc accagtttat cattttaggc ataggacccg tgtct                45

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 12
gcgaacttca gtccaggtca acgtcccttg tttaggcata ggacccgtgt ct          52

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 13
tcccacagaa tgttgtagag ttcaatttta ggcataggac ccgtgtct              48

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 14
aaaacaacaa tatctttttg aacaatatat ttaggcatag gacccgtgtc t           51

<210> SEQ ID NO 15
<211> LENGTH: 26
<212> TYPE: DNA
<213> ORGANISM: Artificial Sequence

```
<220> FEATURE:
<223> OTHER INFORMATION: Description of Artificial Sequence: primer

<400> SEQUENCE: 15
tcaaagtttt cactggagac aagttt                                        26
```